(12) United States Patent
Thompson et al.

(10) Patent No.: US 10,094,794 B2
(45) Date of Patent: Oct. 9, 2018

(54) CHARACTERIZATION OF WRINKLES AND PERIODIC VARIATIONS IN MATERIAL USING INFRARED THERMOGRAPHY

(71) Applicant: The Boeing Company, Chicago, IL (US)

(72) Inventors: Jeffrey G. Thompson, Tacoma, WA (US); Gary E. Georgeson, Tacoma, WA (US); Hong Hue Tat, Redmond, WA (US); Tyler M. Holmes, Seattle, WA (US)

(73) Assignee: The Boeing Company, Chicago, IL (US)

( * ) Notice: Subject to any disclaimer, the term of this patent is extended or adjusted under 35 U.S.C. 154(b) by 260 days.

(21) Appl. No.: 15/374,014

(22) Filed: Dec. 9, 2016

(65) Prior Publication Data

US 2017/0212066 A1    Jul. 27, 2017

Related U.S. Application Data

(63) Continuation-in-part of application No. 15/004,119, filed on Jan. 22, 2016, now Pat. No. 9,519,844.

(51) Int. Cl.
*G01J 5/00* (2006.01)
*G01N 25/72* (2006.01)
(Continued)

(52) U.S. Cl.
CPC ............. *G01N 25/72* (2013.01); *G01J 5/025* (2013.01); *G01J 5/0896* (2013.01); *G06K 9/6267* (2013.01); *H04N 5/2256* (2013.01); *H04N 5/33* (2013.01); *G01J 2005/0048* (2013.01); *G01J 2005/0077* (2013.01); *G01J 2005/0081* (2013.01); *G06T 2207/30248* (2013.01)

(58) Field of Classification Search
CPC ................... G01J 5/02; G01J 5/08; G01J 5/02
USPC .................................. 250/338.1, 341.6, 347
See application file for complete search history.

(56) References Cited

U.S. PATENT DOCUMENTS 6,301,512 B1   10/2001  Motzer
6,751,342 B2 *  6/2004  Shepard ................. G01N 25/72
                                                   250/332

(Continued)

OTHER PUBLICATIONS

U.S. Appl. No. 14/827,788, filed Aug. 17, 2015.

*Primary Examiner* — David Porta
*Assistant Examiner* — Meenakshi Sahu
(74) *Attorney, Agent, or Firm* — Ostrager Chong Flaherty & Broitman P.C.

(57) ABSTRACT

Methods for identifying and quantifying wrinkles in a composite structure by processing infrared image data. The intensity and first and second time derivatives thereof at a particular time can be displayed as thermography line profiles on a graph in which the horizontal axis represents the pixel number across the field of view of an infrared camera. The spatial derivatives of the foregoing thermography line profiles can also be calculated and displayed as a graph. The maximum amplitude (i.e., height) of an out-of-plane wrinkle can be determined using a correlation/calibration curve that is constructed by correlating infrared image data with optical measurement data. In addition, the wavelength and maximum amplitude of an in-plane wrinkle can be measured directly from the thermography line profiles.

20 Claims, 20 Drawing Sheets

(51) Int. Cl.
  *H04N 5/33*   (2006.01)
  *H04N 5/225*  (2006.01)
  *G06K 9/62*   (2006.01)
  *G01J 5/08*   (2006.01)
  *G01J 5/02*   (2006.01)

(56) References Cited

U.S. PATENT DOCUMENTS

| | | |
|---|---|---|
| 7,075,084 B2 | 7/2006 | Thompson et al. |
| 7,119,338 B2 | 10/2006 | Thompson et al. |
| 7,186,981 B2 | 3/2007 | Shepard et al. |
| 7,287,902 B2 | 10/2007 | Safai et al. |
| 7,584,062 B1 | 9/2009 | Tat et al. |
| 7,617,730 B2 | 11/2009 | Georgeson |
| 7,699,521 B2 | 4/2010 | Shepard |
| 7,724,925 B2 * | 5/2010 | Shepard ................. G01N 25/72 382/115 |
| 8,338,787 B1 | 12/2012 | Shelley et al. |
| 8,449,176 B2 | 5/2013 | Shepard |
| 8,499,632 B1 | 8/2013 | Ihn et al. |
| 8,853,634 B2 | 10/2014 | Shelley, Jr. et al. |
| 8,965,100 B2 | 2/2015 | Lin et al. |
| 8,981,771 B2 | 3/2015 | Thompson |
| 9,519,844 B1 * | 12/2016 | Thompson ........... G06K 9/6267 |
| 2012/0219034 A1 | 8/2012 | Nielsen |
| 2014/0333758 A1 | 11/2014 | Wu et al. |
| 2015/0161778 A1 * | 6/2015 | Henderkott ........... G06T 7/0008 348/129 |
| 2016/0221048 A1 | 8/2016 | Thompson et al. |

* cited by examiner

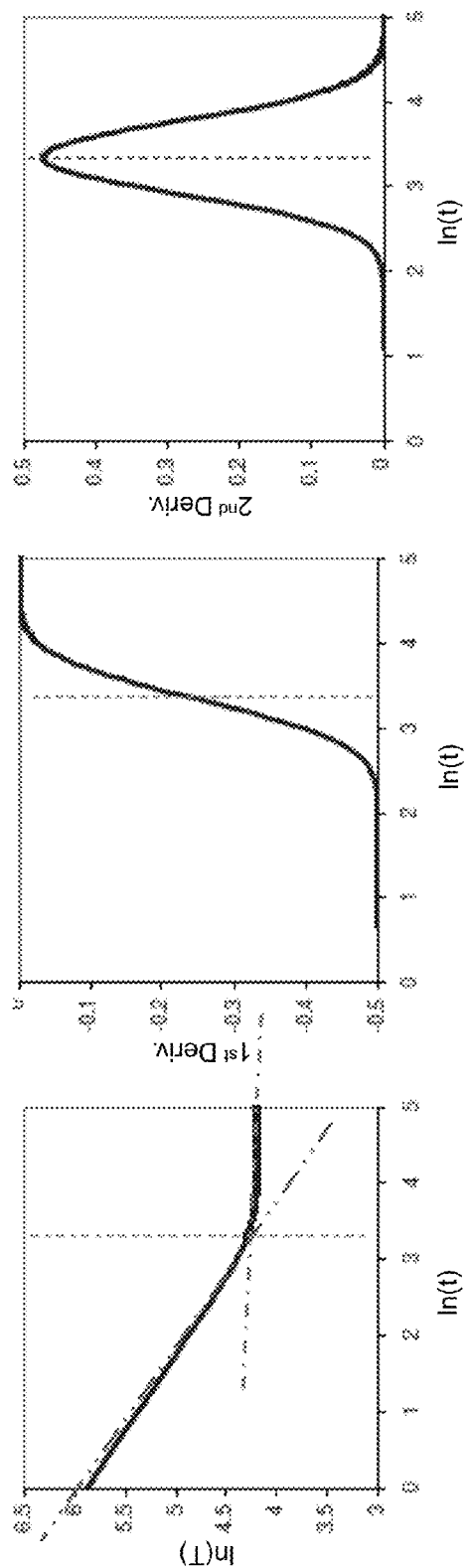

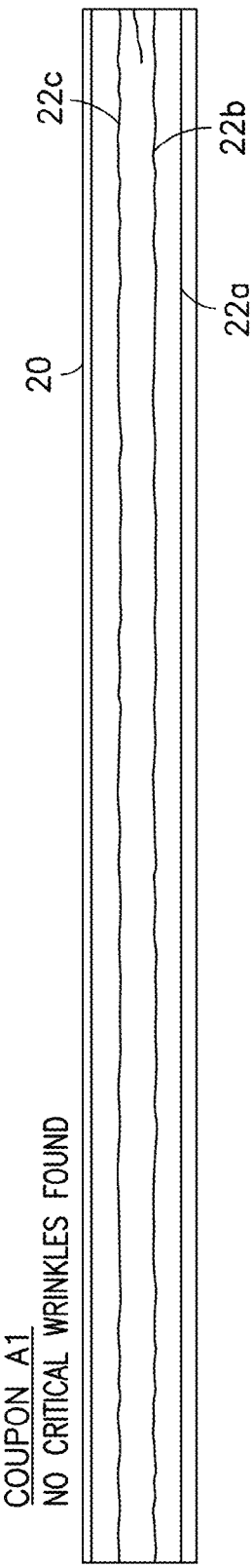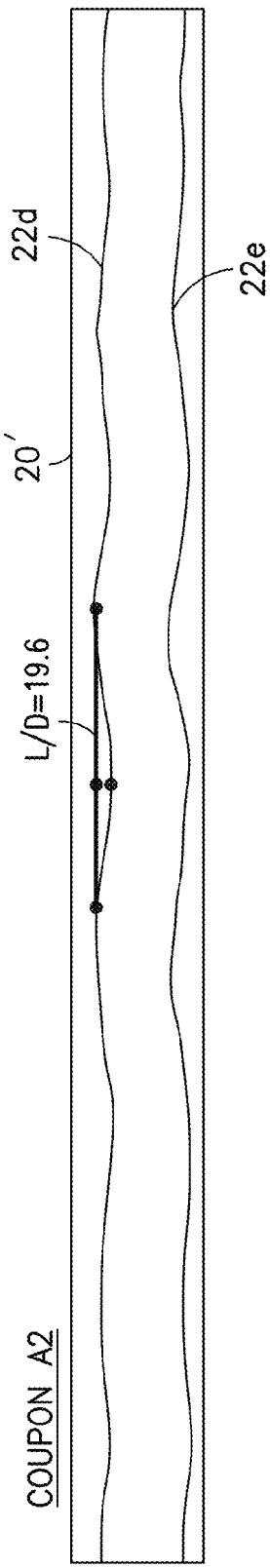
FIG. 10A
FIG. 10B

CHARACTERIZATION OF WRINKLES AND PERIODIC VARIATIONS IN MATERIAL USING INFRARED THERMOGRAPHY

RELATED PATENT APPLICATION

This application is a continuation-in-part of and claims priority from U.S. patent application Ser. No. 15/004,119 filed on Jan. 22, 2016, the disclosure of which is incorporated by reference herein in its entirety.

STATEMENT REGARDING FEDERALLY SPONSORED RESEARCH OR DEVELOPMENT

This invention was made with Government support under Contract No. NNL09AA00A awarded by the National Aeronautics and Space Administration. The Government has certain rights in this invention.

BACKGROUND

This disclosure generally relates to non-destructive inspection of structures or parts, and more particularly to systems and methods for characterizing or evaluating anomalies in material, such as wrinkles in fiber-reinforced plastic material and designed periodic material variations such as low-observable coatings with periodic features for reducing susceptibility to radar detection.

New, lightweight composite materials and designs are being used more extensively in the aerospace industry for commercial aircraft and other aerospace vehicles, as well as in other industries. The structures using these composite materials may be formed using multiple plies or layers of fiber-reinforced plastic material that may be laminated together to form a lightweight, high-strength structure. Fabrication of composite laminate structure for aerospace applications can result in unwanted out-of-plane and/or in-plane wrinkling of plies that can impact performance of the structure based on the size of the wrinkle. Quality assurance and certification for production parts in industries such as the aircraft industry requires that the part be built to meet certain design standards and specifications. For some parts there may be a standard acceptance criteria based on wrinkle size. Accordingly being able to accurately detect and measure the size of any wrinkles in a structure or part is desirable.

Some wrinkles can be identified visually from the surface. However, they cannot be quantified visually, so in an abundance of caution the worst case may be assumed unless means for measuring the size of the wrinkle (often in terms of wavelength L divided by maximum amplitude D) can be provided. Also, wrinkles deeper in the structure cannot be seen visually from the surface at all. Ultrasonic methods have been developed to identify and quantify wrinkles. However, the main drawback of ultrasonic methods is that they cannot "see" beneath a wrinkle (and no access is available to the back side of the structure), so the amount of "good" material is unknown. Therefore, the maximum thickness of a wrinkle from its highest peak to the back surface may have to be assumed. This may result in overly conservative knockdowns of strength predictions, and needless and costly repairs. Another drawback of the ultrasonic method in general is that it takes significant time to collect the data.

Therefore further improvements in methods for non-destructive determination of the size of wrinkles in composite material would be advantageous.

SUMMARY

The subject matter disclosed herein is directed to methods for identifying and quantifying wrinkles in a composite structure by processing infrared image data. In accordance with some embodiments, temperature versus time profiles for all pixels in the field of view of an infrared camera are calculated, enabling thermal signatures to be produced. By comparing the thermal signature of the part under test with the thermal signature of a reference standard representing a similar part having wrinkles of known size and shape, the presence of wrinkles can be detected. The wrinkle wavelength can be determined by measuring the infrared image and applying a transfer function. If the geometric information acquired using infrared thermography does not reach a certain quality factor (for a quality prediction) or is incomplete, an ultrasonic transducer array probe running wrinkle quantification software can be rotated into position and scanned over the wrinkle area. The ultrasonic image data can be combined with the infrared image data to enable an improved quantification of the wrinkle geometry.

The infrared image data captured by infrared cameras can be processed to detect internal defects, particularly wrinkles, in composite structures. A computer system can be programmed to locate and quantify those types of anomalies based on the infrared image data. The system can collect inspection data for detecting wrinkles over large surface areas of the composite structure very rapidly and also quantifying a dimensional parameter of the wrinkles identified. The systems and methods disclosed in detail below apply flash thermography equipment and software in defined ways to identify and measure wrinkles. The infrared camera records the surface temperature as an applied heat pulse diffuses into the surface of the part. The image acquisition time is adjusted to match the thickness and thermal properties of the material under test.

More specifically, the subject matter disclosed in detail below is directed to methods for identifying and quantifying wrinkles in composite structure by processing infrared image data. The three types of images typically available from infrared imaging systems include: (1) intensity; (2) first time derivative of the intensity (hereinafter "first time derivative"); and (3) second time derivative of the intensity (hereinafter "second time derivative"). The intensity and first and second time derivatives thereof at a particular time can be displayed as thermography line profiles on a graph in which the horizontal axis represents the pixel number across the field of view of an infrared camera. The spatial derivatives of the foregoing thermography line profiles can also be calculated and displayed as a graph.

In accordance with other embodiments, the maximum amplitude (i.e., height) of an out-of-plane wrinkle can be determined using a correlation/calibration curve (hereinafter "calibration curve") that is constructed by correlating infrared image data with optical measurement data. A calibration curve is used because the amplitude measurement from the infrared thermography is a temperature-related value, not a spatial value.

In accordance with additional embodiments, the wavelength and maximum amplitude of an in-plane wrinkle can be measured directly from the thermography line profiles because the infrared image has spatial dimensions (i.e., wavelength and maximum amplitude) across the pixels.

One aspect of the subject matter disclosed in detail below is a method for non-destructive inspection of composite structures, comprising: (a) developing a calibration curve for an infrared imaging system based on correlation of infrared image data and optical cross-section measurement data acquired from reference standards made of composite material, at least some of the reference standards having at least one wrinkle; (b) collecting infrared image data from a part made of composite material using the infrared imaging system after completion of step (a); (c) detecting the presence of an out-of-plane wrinkle in the part based on the infrared image data collected in step (b); (d) generating thermographic line profile data based on the infrared image data; (e) measuring a wavelength of the out-of-plane wrinkle in the part based on the thermographic line profile data generated in step (d); and (f) measuring an amplitude of the out-of-plane wrinkle in the part by applying the calibration curve to the thermographic line profile data generated in step (d). This method may further comprise: (g) determining if the part is acceptable based on the measured wavelength and amplitude; and (h) designating the part for repair or further evaluation in response to a determination in step (g) that the part is not acceptable. In accordance with one embodiment, the method further comprises calculating a wrinkle wavelength-to-amplitude ratio using the measured wavelength and amplitude of the out-of-plane wrinkle. In this embodiment, step (g) comprises determining if the wrinkle wavelength-to-amplitude ratio is outside an allowable range, and step (d) comprises calculating a time or spatial derivative of the infrared image data.

Another aspect of the subject matter disclosed in detail below is a method for measuring an out-of-plane wrinkle in a structure made of a composite material, the method comprising: (a) developing a calibration curve for an infrared imaging system based on correlation of infrared image data and optical cross-section measurement data acquired from reference standards made of composite material, at least some of the reference standards having at least one wrinkle; (b) acquiring infrared image data from an inspected area on a surface of the structure using an infrared camera of the infrared imaging system, the infrared image data being indicative of the presence of an out-of-plane wrinkle under the surface of the inspected area; (c) generating thermographic line profile data based on the infrared image data; (d) processing the thermographic line profile data to estimate a value of a first wrinkle dimensional parameter of the out-of-plane wrinkle; (e) processing the thermographic line profile data to estimate a value of a second wrinkle dimensional parameter of the out-of-plane wrinkle based in part on the calibration curve; (f) calculating a value of a wrinkle parameter which is a function of the first and second wrinkle dimensional parameters; and (g) determining a status of the composite structure in dependence on whether the value of the wrinkle parameter calculated in step (f) is inside or outside an allowable range of values. In some embodiments, step (c) comprises calculating a time or spatial derivative of the infrared image data. In one implementation, the first wrinkle dimensional parameter is wrinkle wavelength, the second wrinkle dimensional parameter is wrinkle maximum amplitude, and the wrinkle parameter is a ratio of the wrinkle wavelength to the wrinkle maximum amplitude.

A further aspect of the subject matter disclosed in detail below is a method for measuring an in-plane wrinkle in a composite structure, comprising: (a) moving an infrared camera to a location whereat a field of view of the infrared camera encompasses an inspection area on a surface of the composite structure; (b) activating at least one flash lamp to output light that illuminates at least portions of the inspection area; (c) activating the infrared camera to acquire infrared image data while the field of view of the infrared camera encompasses at least the inspection area; (d) processing the infrared image data to identify selected points along an in-plane wrinkle; and (e) determining a wavelength and a maximum amplitude of the in-plane wrinkle based on the selected points using image processing software.

Yet another aspect of the subject matter disclosed in detail below is a method for calibrating an infrared imaging system, comprising: (a) forming a first reference standard made of a type of composite material and having a wrinkle; (b) forming a second reference standard made of the same type of composite material and not having a wrinkle; (c) collecting first infrared image data from the first reference standard; (d) collecting second infrared image data from the second reference standard; (e) generating first thermographic line profile data based on the first infrared image data; (f) generating second thermographic line profile data based on the first infrared image data; (g) calculating a change in the first thermographic line profile data along a line in the first reference standard; (h) calculating a change in the second thermographic line profile data along a line in the second reference standard; (i) calculating a difference between the respective changes; (j) cutting the first and second reference standards to expose cross sections, wherein the cross section of the first reference standard intersects the wrinkle; (k) imaging the exposed cross sections of the first and second reference standards to produce respective optical cross sections; (l) measuring an amplitude of the wrinkle which appears in the optical cross section of the first reference standard; (m) calculating a conversion factor based on the difference calculated in step (i) and the amplitude measured in step (l); and (n) constructing a calibration curve using the conversion factor. In accordance with various embodiments, the changes in the first and second thermographic line profile data are differences between respective time derivatives of intensity or respective spatial derivatives at respective spatial points along the lines in the first and second reference standards.

A further aspect of the subject matter disclosed in detail below is an infrared imaging system comprising a computer configured to convert infrared image data to a wrinkle maximum amplitude measurement value based on a calibration curve that correlates infrared image data indicative of an out-of-plane wrinkle to optical cross-section measurement data indicative of an out-of-plane wrinkle. In one embodiment, converting the infrared image data to the wrinkle maximum amplitude measurement value comprises generating thermographic line profile data based on the infrared image data and then processing the thermographic line profile data to estimate the wrinkle maximum amplitude measurement value based in part on the calibration curve.

Some of the benefits provided by the infrared thermography (IRT) technology disclosed herein include very rapid inspection (faster than array-based ultrasound inspection) and the ability to see beneath wrinkles to quantify "good" material, thereby reducing knockdown factors and buying off more material; and IRT can be used to replace ultrasound testing in some cases where part thickness is within the useful range (up to ¼" or so) of the infrared imaging system.

Other aspects of systems and methods for using infrared thermography to characterize in-plane and out-of-plane wrinkles and other periodic variations in material (e.g., composite material) are disclosed below.

BRIEF DESCRIPTION OF THE DRAWINGS

FIG. 3A is a graph of the logarithm of the surface temperature of a typical composite panel versus the logarithm of time following exposure to a heat pulse.

FIG. 3B is a graph of the first time derivative of the logarithm of the surface temperature presented in FIG. 3A versus the logarithm of time.

FIG. 3C is a graph of the second time derivative of the logarithm of the surface temperature presented in FIG. 3A versus the logarithm of time.

FIG. 10A is a diagram representing a micrograph of sectioned "wrinkle-free" (i.e., free of critical out-of-plane wrinkles) composite material in a coupon A1, the micrograph having superimposed thereon boundary lines representing estimated interfaces between plies.

FIG. 10B is a diagram representing a micrograph of sectioned composite material in a coupon A2 having out-of-plane wrinkles, the micrograph having superimposed thereon boundary lines representing estimated interfaces between plies.

Reference will hereinafter be made to the drawings in which similar elements in different drawings bear the same reference numerals.

DETAILED DESCRIPTION

Figure 1:
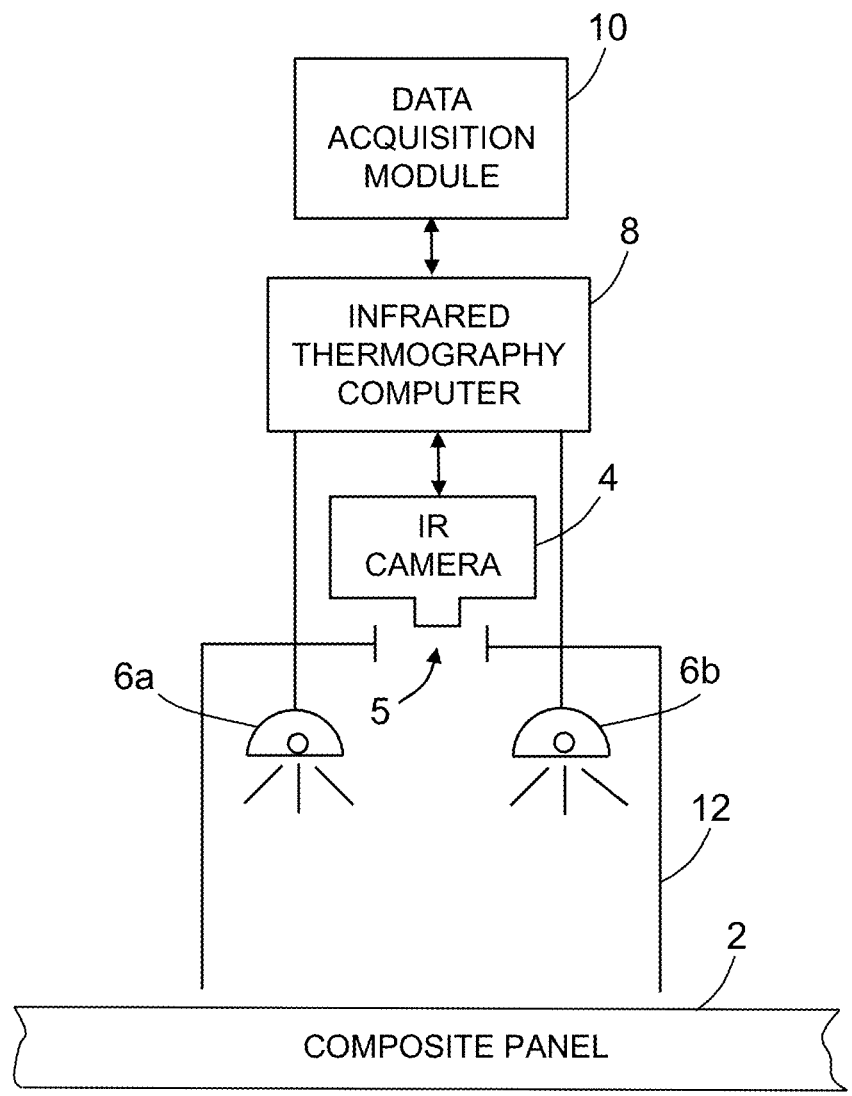
FIG. 1 is a block diagram identifying some components of a system for thermographic imaging of a fuselage section.

For the purpose of illustration, systems and methods for active (i.e., pulsed) infrared thermographic inspection of structures made of composite material (e.g., a composite laminate made of fiber-reinforced plastic) and analysis of the collected thermographic data using software tools that enable very rapid identification and quantification of wrinkles in composite structures will now be described in detail. Such systems and methods can achieve rapid infrared thermographic inspection of large composite structures (e.g., curved cylinder-like workpieces made of composite material). For the sake of illustration, systems and methods for infrared thermographic inspection of barrel-shaped (e.g., half or full barrel) fuselage sections made of composite material will be disclosed in detail below. However, it should be appreciated that the apparatus disclosed herein can be employed in the infrared thermographic inspection of composite structures other than fuselage sections.

In accordance with embodiments disclosed in detail below, the inspection apparatus comprises flash lamps and infrared cameras, which are employed to thermographically inspect large composite structures in a non-contact, non-couplant manner. The flash lamps and infrared cameras may be supported by one or more robots that travel along tracks. As used herein, the term "tracks" encompasses rails, grooves, guide surfaces, and equivalents thereof. A track may be straight (i.e., linear) or curved. In the alternative, the flash lamps and infrared cameras could be mounted on a moving gantry (i.e., a platform that spans the composite structure and travels along parallel tracks). In this manner, the thermographic hardware (flash lamps and infrared cameras) can be moved along the surface of a composite structure to ensure access for inspection of the entire part.

Infrared thermography methods and devices make it possible to perform non-destructive testing of a material to detect defects, variations in the properties of the material, or differences in thickness of a coating or layer of the material. Infrared imaging can detect local variations in thermal diffusivity or thermal conductivity at or beneath the surface of the material.

Active thermography is used to nondestructively evaluate samples for sub-surface defects. It is effective for uncovering internal bond discontinuities, delaminations, voids, inclusions, and other structural defects that are not detectable by visual inspection of the sample. Generally, active thermography involves heating or cooling the sample to create a difference between the sample temperature and the ambient temperature and then observing the infrared thermal image that emanates from the sample as its temperature returns to ambient temperature. An infrared camera is used because it is capable of detecting any anomalies in the cooling behavior, which would be caused by sub-surface defects blocking the diffusion of heat from the sample surface to the sample's interior. More particularly, these defects cause the surface immediately above the defect to cool at a different rate than the surrounding defect-free areas. As the sample cools, the infrared camera monitors and records an image time sequence indicating the surface temperature, thereby creating a record of the changes in the surface temperature over time.

Typically, the surface of the material is heated using a flash lamp and after a fixed period of time, a thermal image is taken of the surface of the heated material. Systems for thermographic heating typically employ xenon flashtubes and off-the-shelf photographic power supplies for sample excitation. An infrared camera images the infrared spectral radiance from the surface of the material, which is representative of the temperature of the surface of the material. Differences in temperature of the surface of the material indicate differing thermal characteristics of the material. These variations in thermal characteristics of the material indicate a possible material defect or the inclusion of a foreign material.

Structural thickness and stack-up geometry needed for infrared signature processing are obtained by knowing the exact location of the infrared camera's field of view on the surface of the fuselage section.

FIG. 1 is a block diagram identifying some components of a system for thermographic imaging of a panel 2 made of composite material (e.g., fiber-reinforced plastic material). This infrared imaging system comprises a digital infrared camera 4 having a lens that is directed through a camera lens aperture 5 in a hood 12, which is designed to form a hooded enclosure adjacent to the surface being inspected. A pair of flash lamps 6a and 6b are disposed inside and in fixed spatial relationship to the hood 12. The flash lamps 6a and 6b produce flashes of light in response to trigger signals from an infrared thermography computer 8, which also controls operation of the infrared camera 4. One example of a type of infrared camera 4 suitable for use with at least some of the embodiments disclosed herein includes a focal plane array device configured to act as a spectral radiometer. Further details concerning other components that may be included in a flash lamp assembly of a type comprising an infrared camera, a pair of flash lamps and a hood can be found, for example, in U.S. Pat. No. 7,186,981.

In accordance with one method of infrared thermographic inspection, first the flash lamps 6a and 6b are triggered to transfer heat to the composite material of the panel 2. Preferably, during cooling of the composite material, the infrared camera 4 is triggered periodically to capture successive digital images of the varying spectral radiance of the heated portion of the panel 2. Preferably, the thermally excited (heated) region of the composite material being inspected will cool monotonically after the excitation source is removed until the composite material reaches thermal equilibrium with its surroundings. The thermal response of any point on the surface of the composite material during the time interval immediately after heating will decay in such a manner that the natural logarithm of the temperature-time response of a defect-free sample, as it cools, is a function that can be approximated by a straight line.

The digital infrared image data captured by infrared camera 4 is received by the infrared thermography computer 8 for processing. The infrared thermography computer 8 is programmed to process infrared image data to detect and locate material anomalies. The infrared image data may be displayed on a display monitor (not shown in FIG. 1), which may be integrated with or separate from infrared thermography computer 8.

In accordance with the embodiment depicted in FIG. 1, the infrared thermography computer 8 may have digital image acquisition capabilities to convert the infrared image data from the infrared camera 4 to a format that can be analyzed and mathematically manipulated by the infrared thermography computer 8. An optional data acquisition module 10 may be incorporated in or separate from (as depicted in FIG. 1) the infrared thermography computer 8. The data acquisition module 10 may be used if the infrared camera 4 captures multiple spatially different images to generate a complete mosaic image of the surface of the composite structure when the latter is too large to fit in a single image frame. The infrared thermography computer 8 may be further programmed to analyze the infrared image data captured by the infrared camera 4. In particular, the time history of the surface temperature response of the composite panel 2 as it returns to room temperature can be analyzed to detect the presence of defects in the composite material.

In the context of the specific application of inspecting aircraft fuselage sections, a non-destructive inspection system may comprise means for scanning the skin of the fuselage section from a vantage point external to the fuselage section and means for scanning substructure, such as stiffeners attached to the inside of the fuselage section. The means for scanning stiffeners on the inside of a fuselage section can work in concert and concurrently with the means that scan the fuselage section externally. In the alternative, the external and internal scanning can be performed at different times and/or at different places. The fuselage sections can be scanned externally before or after the stiffeners have been attached. In the embodiments disclosed below, the internal scanning means comprise ultrasonic transducer arrays, while the external scanning means comprise infrared cameras.

Figure 2:
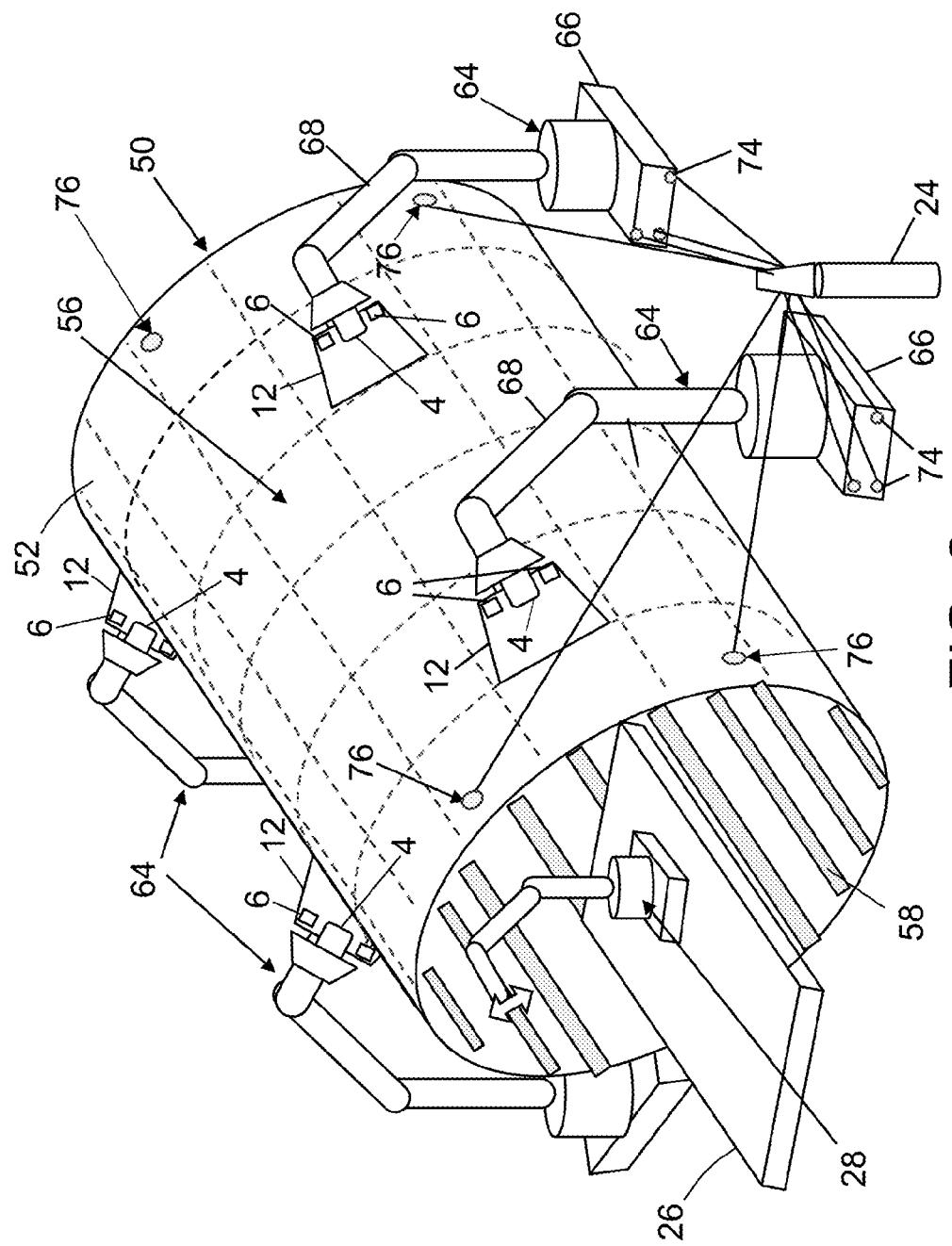
FIG. 2 is a diagram representing an isometric view of a full-barrel fuselage section being inspected by an infrared imaging system having multiple robots in accordance with one embodiment. A laser tracker determines the locations of the robots relative to the fuselage section using optical targets attached to the fuselage section and to the robot bases.

FIG. 2 depicts a full-barrel fuselage section 50 (made of composite material) being inspected by a non-destructive inspection system comprising multiple robots 64 equipped with infrared thermography assemblies in accordance with one embodiment. Each robot 64 comprises a movable robot base 66 and an articulated robotic arm 68 having a proximal end coupled to the robot base 66. Each robot base 66 may be mounted to a mobile holonomic crawler vehicle or coupled to a linear track (not shown in FIG. 2). A respective infrared thermography assembly is coupled to a distal end of each robotic arm 68. Each infrared thermography assembly comprises an infrared camera 4 and two or more flash lamps 6 attached inside a hood 12. Each hood 12 may be sized to cover a respective square area 56 on the outer surface 52 of the fuselage section 50. The infrared image data acquired from adjacent square areas 56 can be stitched together based on measurements of the respective locations of the robot base 66 using a laser tracker 24 and respective movements of the robotic arms 68 using encoders incorporated in the robot 64. The stitching process may be performed on a real-time basis or may be performed at a later time.

In accordance with one embodiment, a laser tracker 24 is used to determine the locations of the robot bases 66 relative to the fuselage section 50. This is accomplished using optical targets 74 attached to the robot bases 66 and optical targets 76 attached to the fuselage section 50. Optical targets 76 may comprise spherically mounted retroreflectors, which will be described in more detail below. The optical targets 76 may be inserted in holes formed at predetermined locations about the outer surface 52 of the fuselage section 50. The holes in the fuselage section 50 may be components of a part reference system, such as a determinant assembly coordinate system, in which parts are referenced to each other (as opposed to the parts being referenced to assembly tooling). The part reference system suitably indexes the location of each of the holes in three dimensions.

The system depicted in FIG. 2 can be used to acquire infrared image data representing characteristics of the internal structure of the composite material. The acquired infrared image data can be processed in different ways using the following equations:

$$\Delta T(t) = \frac{Q}{e\sqrt{\pi t}}$$

$$e = \sqrt{k\rho C}$$

$$\ln(\Delta T) = \ln\left(\frac{Q}{e\sqrt{\pi}}\right) - 0.5\ln(t)$$

where T is surface temperature; t is time; e is the thermal effusivity or resistance to heat flow; Q is the input energy; k is the thermal conductivity; $\rho$ is the density; and C is the heat capacity. A low thermal effusivity means that diffusing heat travels quickly through the material (e.g., metals), so that the temperature change across the thickness of the material is small; a high thermal effusivity means that diffusing heat travels slowly through the material (e.g., composites), so that the temperature change across the thickness of the material is large.

Figure 3:
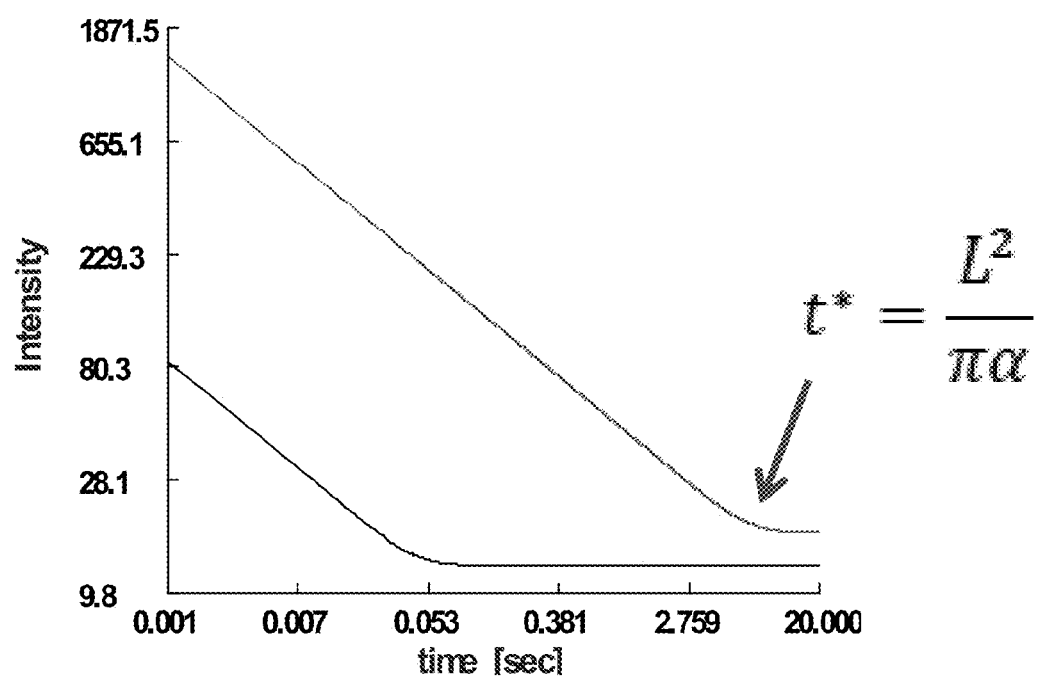
FIG. 3 is a graph of intensity (i.e., surface temperature) versus time (using logarithmic scales) for two composite panels following exposure to a heat pulse.

FIG. 3 is a graph of intensity (i.e., surface temperature) versus time (using logarithmic scales) for two composite panel samples following exposure to a heat pulse. The break from a slope of −0.5 indicates that the diffusing heat has reached an interface. The thickness L of the material can be calculated based on the time t* at which that break occurs using the following equation:

$$t^* = \frac{L^2}{\pi\alpha}$$

where $\alpha$ is the thermal diffusivity or rate of heat flow ($\alpha = k/\rho C$);

FIG. 3A is a graph of the logarithm of the surface temperature of a typical composite panel versus the logarithm of time following exposure to a heat pulse. FIG. 3B is a graph of the first time derivative of the logarithm of the surface temperature presented in FIG. 3A versus the logarithm of time. FIG. 3C is a graph of the second time derivative of the logarithm of the surface temperature presented in FIG. 3A versus the logarithm of time. These curves spread when the composite material underneath the surface area exposed to the heat pulse during infrared thermography contains wrinkles.

Figure 4A:
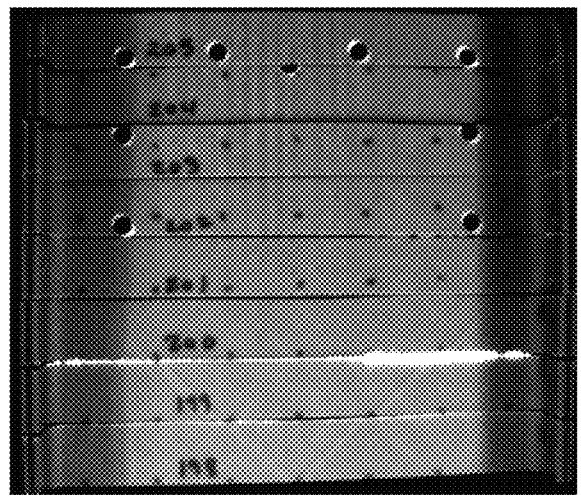
FIG. 4A is a raw infrared image of a wrinkled composite specimen.
Figure 4B:
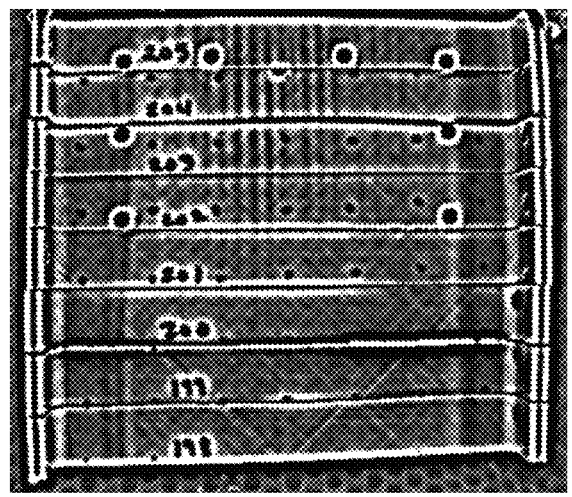
FIG. 4B shows the result when the raw infrared image shown in FIG. 4A is high-pass filtered.
Figure 4C:
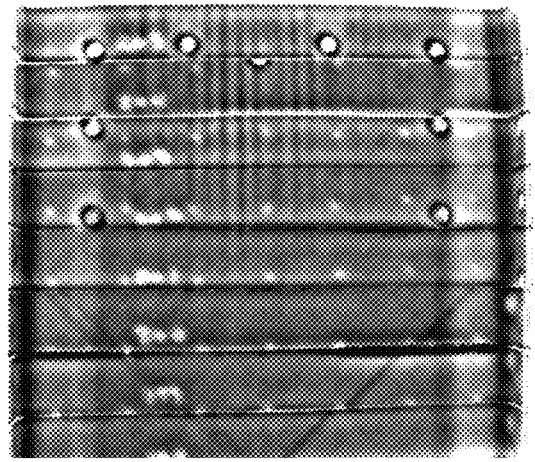
FIG. 4C shows the result when the raw infrared image shown in FIG. 4A undergoes first-time-derivative processing.
Figure 4D:
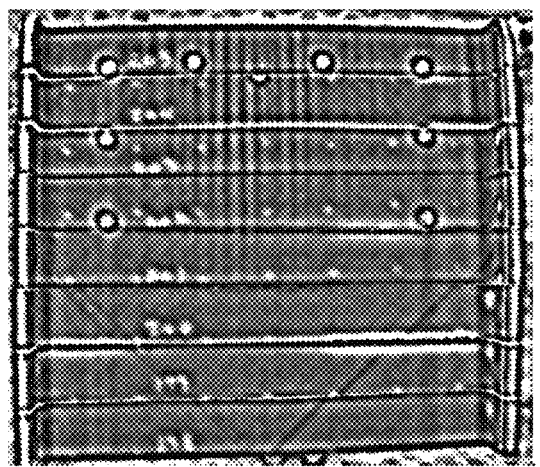
FIG. 4D shows the result when the first-time-derivative infrared image shown in FIG. 4C is high-pass filtered.
Figure 4E:
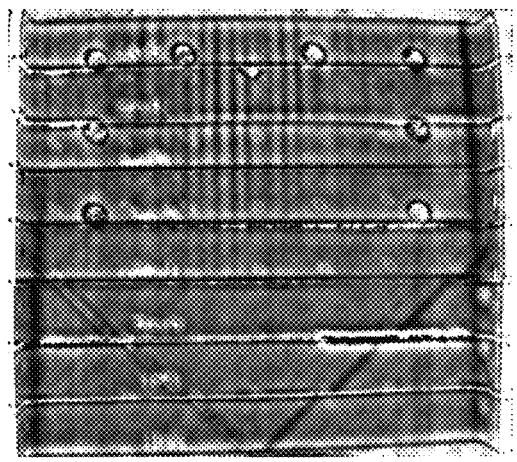
FIG. 4E shows the result when the first-time-derivative infrared image shown in FIG. 4C undergoes second-time-derivative processing.
Figure 4F:
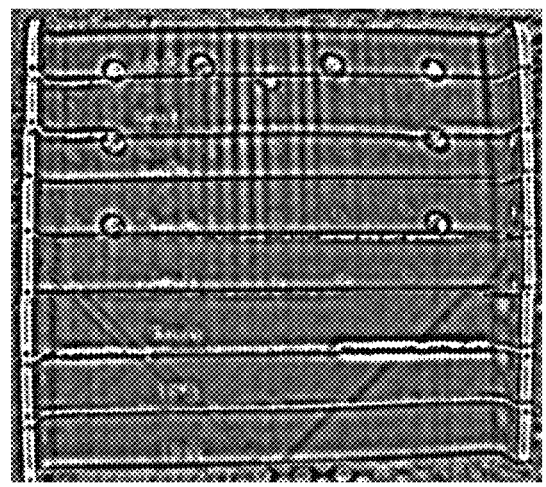
FIG. 4F shows the result when the second-time-derivative infrared image shown in FIG. 4E is high-pass filtered.

FIGS. 4A through 4F present infrared image data acquired from wrinkled composite specimens. Data was collected with an infrared imaging camera, such as an infrared camera available from Thermal Wave Imaging, Inc. (Ferndale, Mich.). Data collected by a Thermal Wave Imaging infrared camera may be processed using a known thermographic signal reconstruction (TSR®) method. The images seen in FIGS. 4A through 4F show that wrinkles are detectable very rapidly using infrared thermography. FIG. 4A is a raw infrared image of a wrinkled composite specimen. FIG. 4B shows the result when the raw infrared image shown in FIG. 4A is high-pass filtered. FIG. 4C shows the result when the raw infrared image shown in FIG. 4A undergoes first-time-derivative processing. FIG. 4D shows the result when the first-time-derivative infrared image shown in FIG. 4C is high-pass filtered. FIG. 4E shows the result when the first-time-derivative infrared image shown in FIG. 4C undergoes second-time-derivative processing. FIG. 4F shows the result when the second-time-derivative infrared image shown in FIG. 4E is high-pass filtered.

Wrinkles can be imaged from both sides (OML and IML) of a composite part. High intensity on one side corresponds to low intensity on the opposite side. There will be cooler temperature measurement at wrinkle peak, where there is a higher fiber/resin ratio, and hotter temperature measurement at wrinkle valley, where there is a lower fiber/resin ratio.

Off-the-shelf software can be modified to do a search routine for finding wrinkles by creating thermal signatures that can be used to rapidly and automatically indicate the presence of wrinkle indicia in an infrared image and then starting a process to find and quantify those wrinkles by comparing the acquired thermal signatures to reference thermal signatures stored in a reference database. The hardware where the reference database resides is a non-transitory tangible computer-readable medium.

Figure 5A:
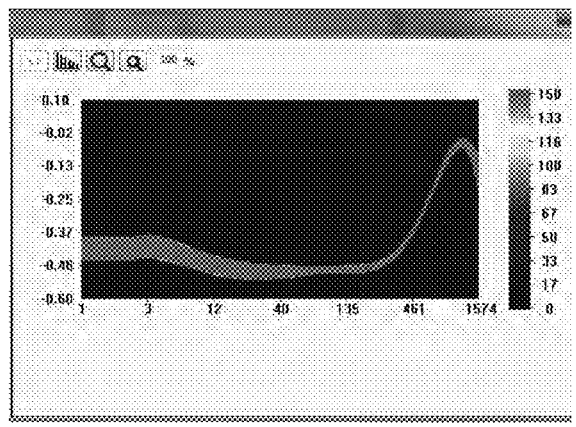
FIG. 5A is a screenshot from a display monitor which includes display of a graph of the first time derivative of the surface temperature in a wrinkle-free region of a composite panel versus time (using logarithmic scales) for all pixels corresponding to that wrinkle-free region, the result being referred to herein as a "no wrinkle signature". (Although not apparent from FIGS. 5A-5C, in actuality such signatures may be displayed in color.)

FIG. 5A is a screenshot from a display monitor which includes display of a graph of the first time derivative of the surface temperature in a wrinkle-free region of a composite panel versus frame number (using logarithmic scales) for all pixels corresponding to that wrinkle-free region, the result being referred to herein as a "no wrinkle signature". (Although not apparent from FIGS. 5A-5C, in actuality such signatures may be displayed in color.)

Figure 5B:
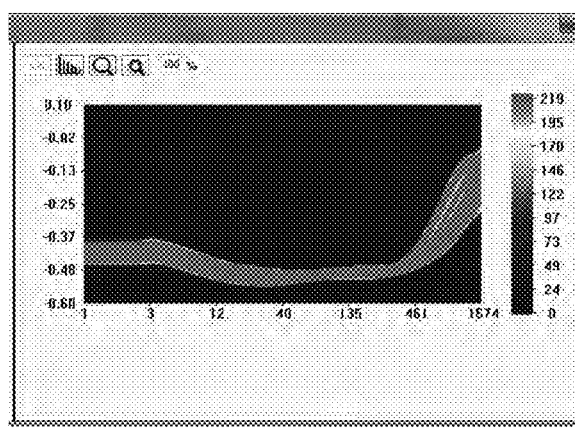
FIG. 5B is a screenshot from a display monitor which includes a graph of the first time derivative of the surface temperature in a wrinkled region of the same composite panel versus time (using logarithmic scales) for all pixels corresponding to that wrinkled region, the result being referred to herein as a "wrinkle signature".

FIG. 5B is a screenshot from a display monitor which includes a graph of the first time derivative of the surface temperature in a wrinkled region of the same composite panel versus frame number (using logarithmic scales) for all pixels corresponding to that wrinkled region, the result being referred to herein as a "wrinkle signature".

Figure 5C:
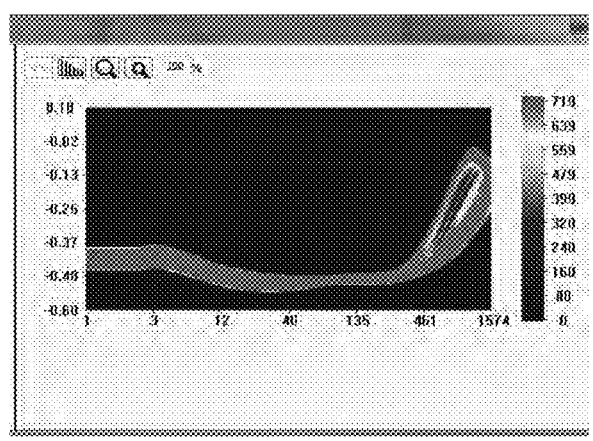
FIG. 5C is a screenshot from a display monitor which includes a graph of the first time derivative of the surface temperature versus time (using logarithmic scales) when the wrinkle and wrinkle-free signatures are superimposed for the purpose of automatic defect recognition.

FIG. 5C is a screenshot from a display monitor which includes a graph of the first time derivative of the surface temperature versus frame number (using logarithmic scales) when the wrinkle and wrinkle-free signatures are superimposed for the purpose of automatic defect recognition.

In each of FIGS. 5A through 5C, the horizontal axis is the number of image frames acquired after the flash lamp is activated. Frames can be converted to time by dividing by the frame rate of the camera. The typical frame rate is 60 or 120 Hz, but can be changed if required to permit longer examination times. The superposition of the wrinkle/no wrinkle signatures seen in FIG. 5C occurs when those two regions of interest are combined. For automatic defect recognition purposes, one would expect to see the no wrinkle signature. If the wrinkle signature occurs, then it is obvious that there is a wrinkle in the composite part under test.

Characterization of Out-of-Plane Wrinkles

Figure 6:
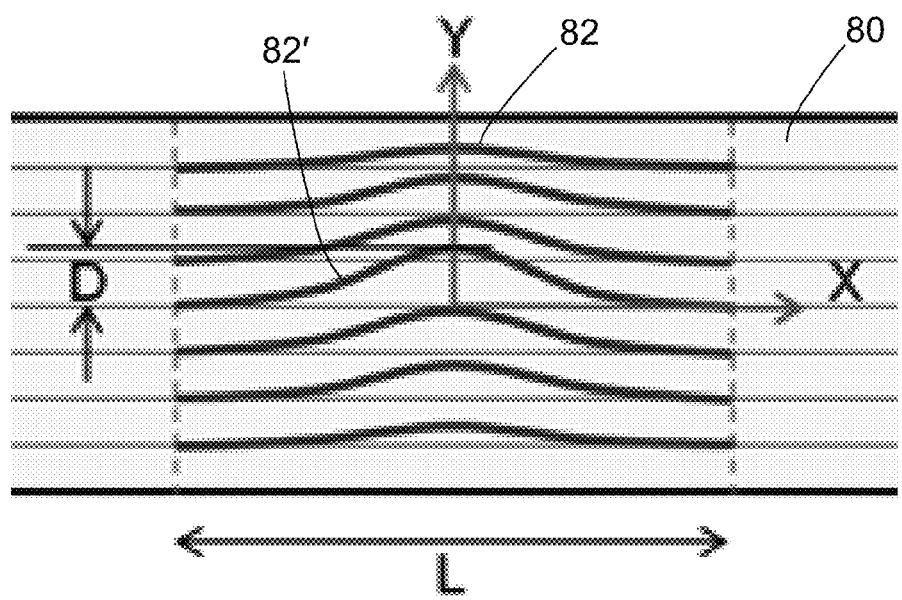
FIG. 6 is a diagram representing an idealized wrinkle profile in a composite laminate comprising a multiplicity of plies.
Figure 7:
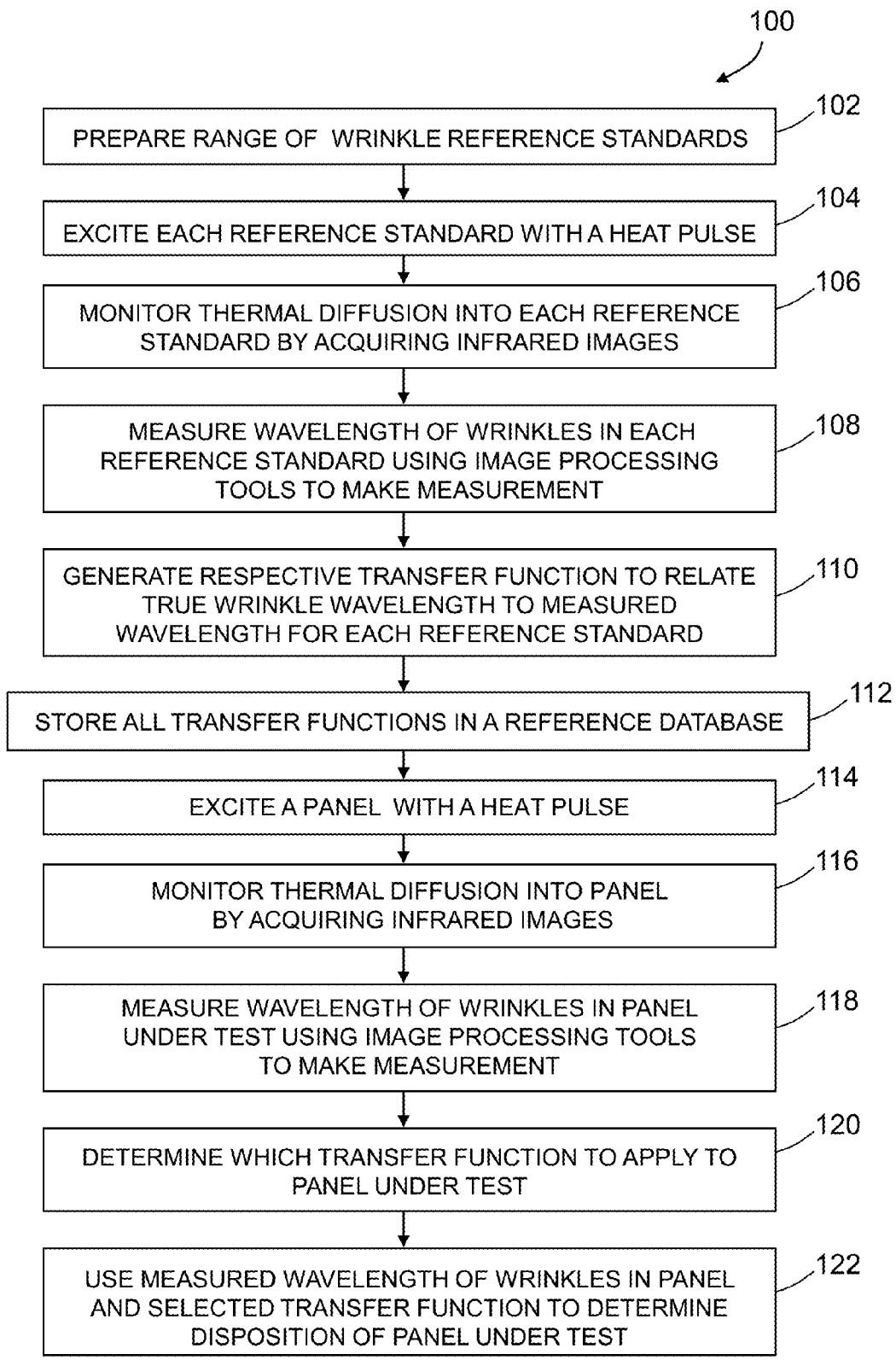
FIG. 7 is a flowchart identifying steps of a method for infrared thermographic inspection in accordance with one embodiment.

FIG. 6 is a diagram representing an idealized wrinkle profile in a composite laminate comprising a multiplicity of plies 80. This idealized wrinkle profile includes a multiplicity of boundary lines 82 that represent estimated interfaces between plies. The boundary line 82' traces out a simple cosine function that is based on the wavelength L and maximum amplitude D of the wrinkle. In accordance with one embodiment, the profile can be represented by the following equations:

$$y'(x, y) = y + \frac{h}{2}\left[1 + \cos\left(\frac{2\pi x}{L}\right)\right]$$

$$h = D\left[1 - \left|\frac{2y}{T}\right|\right]$$

where T is the total thickness of the laminate.

One method for detecting and characterizing wrinkles in composite material uses a combination of infrared thermographic inspection and ultrasonic inspection. First, infrared thermography can be used to identify the presence of a wrinkle using thermal signatures. The wavelength of the wrinkle can be measured using infrared image processing. Thermography can measure the wavelength, but cannot measure the amplitude. So, if a rapid thermography detection is made, a more time-consuming special ultrasonic scan could be performed to assess the amplitude. More specifically, once an area having wrinkles has been located using infrared thermography and the wavelength of the wrinkles are estimated, an ultrasonic transducer array can be used to scan the identified region of interest to acquire ultrasonic image data including the amplitude of the wrinkles.

The infrared image data captured by the infrared cameras can be processed to detect internal defects, particularly wrinkles, in composite structures. A computer system can be programmed to locate and quantify those types of anomalies based on at least the infrared image data. The system can collect infrared image data for detecting wrinkles over large surface areas of the composite structure very rapidly and also quantifying a dimensional parameter of the wrinkles identified.

The systems and methods disclosed in detail in this section apply flash thermography equipment and software (e.g., software commercially available from Thermal Wave Imaging, Inc., Ferndale, Mich.) in defined ways to identify and measure out-of-plane wrinkles. The infrared camera records the surface temperature as an applied heat pulse diffuses into the surface of the part. The image acquisition time is adjusted to match the thickness and thermal properties of the material under test. Temperature versus time profiles for all pixels in the field of view are calculated, enabling thermal signatures to be produced. By comparing the thermal signature of the part under test with the thermal signature of a reference representing a similar part having wrinkles, the presence of wrinkles can be detected. For example, the thermal signature may be based on a logarithmic first time derivative of temperature versus time (i.e., $d[\ln(T)]/d[\ln(t)]$) for each pixel in a selected area on the surface of the part. In accordance with some embodiments, the thermal images are enhanced by viewing an image created by intensities related to the second time derivative (i.e., $d^2[\ln(T)]/d^2[\ln(t)]$ and applying a high pass filter to the image.

The wrinkle wavelength can be determined by measuring the infrared image and applying a correction factor (referred to hereinafter as a "transfer function") that accounts for any effects of the configuration of the composite part being measured (such as the heat loss or smearing of the thermal data in thicker composite parts). If the geometric information acquired using infrared thermography does not reach a certain quality factor (for a quality prediction) or is incomplete or needs to be further quantified, an ultrasonic transducer array probe running wrinkle quantification software can be rotated into position and scanned over the wrinkle area. The ultrasonic image data can be combined with the infrared image data to enable an improved quantification of the wrinkle geometry. (The infrared image data may provide information about the amount of good material under a wrinkle that the ultrasonic image data cannot provide.) More specifically, ultrasonic inspection can be used to generate digital data representing a 3-D model of a wrinkle that has been previously detected using infrared thermography. The wrinkle amplitude D could then be determined based on that 3-D model. Then the ratio L/D along a wrinkle line can be estimated. That information can be sent, along with orientation information, to a plug-in for a finite element-based stress model using structural codes or to a stress analyst to determine the impact of the wrinkles on performance of the inspected workpiece or part.

It may also be possible to generate a so-called "thermal B-scan" image which could be used to estimate the maximum amplitude (i.e., height) of the wrinkle. The thermal B-scan could be automatically checked for indications that there is "good" material underneath the wrinkle. Using this information, it may possible to estimate the wrinkle amplitude D and wrinkle thickness T (i.e., the number of plies of the composite laminate which are disoriented).

Once an area has been fully characterized for input to stress models, the infrared imaging system can be moved to the next area to be inspected. The steps in the process can be repeated for each area until the entire composite structure has been inspected or until a structure with a thickness in the appropriate range has been inspected.

In accordance with some embodiments, the IRT wrinkle wavelength measurement process employs a standard thermal signature database comprising respective sets of standard thermal signatures acquired from composite material of different known thicknesses having wrinkles of known size and shape. Preferably, reference standards of composite material can be fabricated which have artificial wrinkles with known dimensions (i.e., known wavelength, amplitude, thickness, and depth). In the alternative, a range of wrinkles can be gathered from production.

Figure 8:
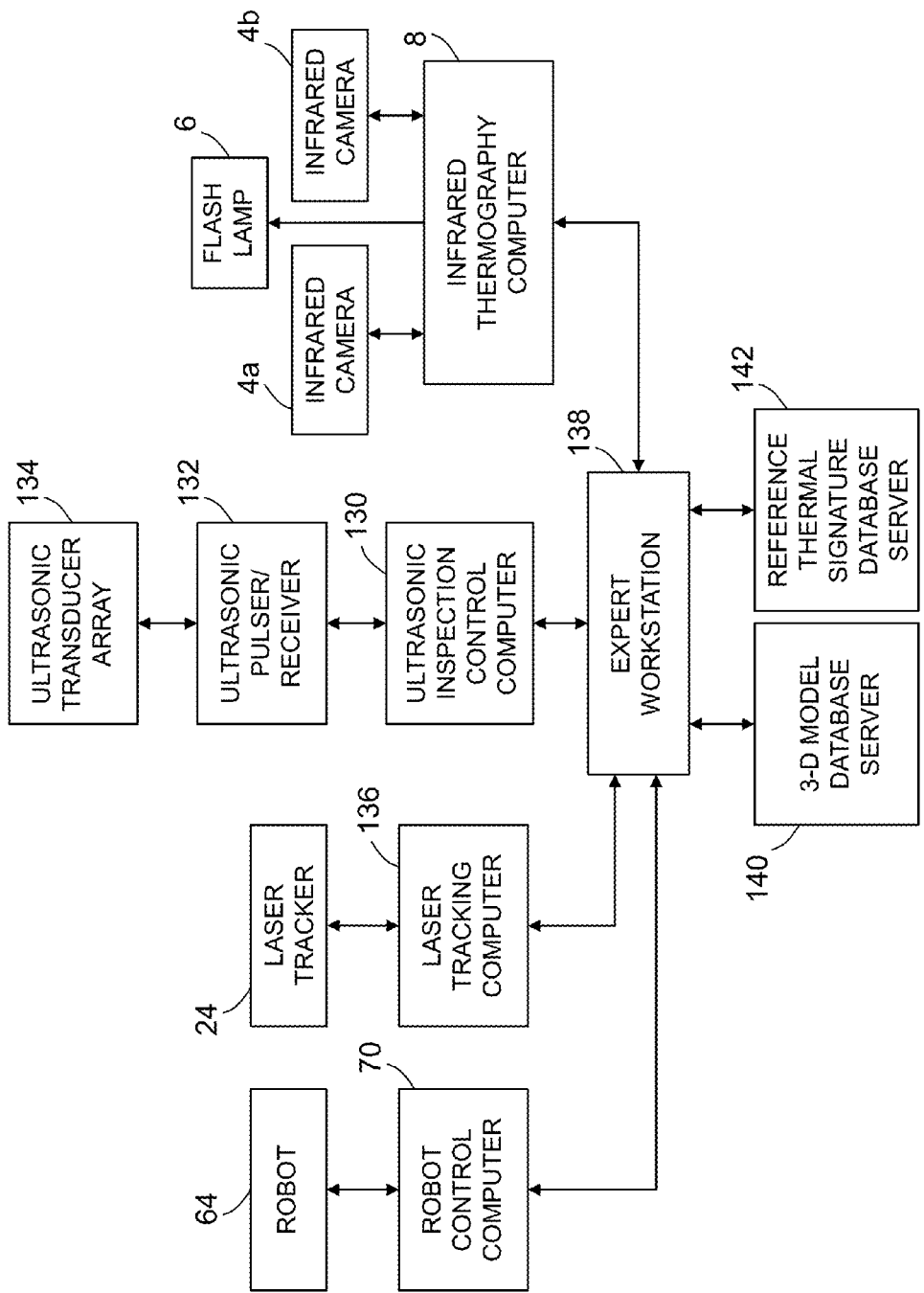
FIG. 8 is a block diagram identifying some components of a system for non-destructive inspection of large composite structures in accordance with some embodiments.

FIG. 8 is a flowchart identifying steps of a method 100 for infrared thermographic inspection in accordance with one embodiment. Before inspection is started, a multiplicity of reference standards having wrinkles with a range of amplitudes, wavelengths and depths are prepared (step 102), e.g., by fabrication of reference standards having wrinkles with programmed (i.e., known) amplitude and wavelength or by collecting production samples. In the alternative, one could use micro-sectioned parts with wrinkles in the absence of a wrinkle standard.

Each reference standard is then excited with a heat pulse (step 104). Subsequent thermal diffusion of heat into each reference standard by acquiring infrared images (step 106). Wrinkles disrupt the heat flow. Although the thickness of material can be constant, the orientation of the fibers and the localized resin content disrupt the flow in different ways. At locations where the out-of-plane distortion of the fibers is nearest the surface monitored by the infrared camera, the surface will be cool. At locations where the resin pool (caused by the wrinkle) is closest to the surface, the surface will be hot. After the raw infrared images have been captured, they are stored in a reference database. In many cases, it is recommended that the raw infrared image data be processed with a method such as first-time-derivative processing. In addition, the first-time-derivative image data can be processed using second-time-derivative processing. All of this image data is stored in the reference database.

Still referring to FIG. 8, using either the first- or second-time-derivative image data, the wavelength of the wrinkles in each reference standard is measured using image processing tools to make the measurement in a well-known manner (step 108). (Preferably the wavelength is measured from one positive peak to another positive peak in the wrinkles.) The available range of wrinkle specimens can be used to define the minimum detectable wrinkle amplitude and wavelength. There is a minimum amplitude that cannot be detected, since the out-of-plane distortion is too small to cause the surface temperature variation. This amplitude sets the detectable amplitude. As long as the minimum amplitude is above the detection threshold, the necessary wrinkles can be detected and the rest ignored. High-pass filters can be used to enhance the detail of the waves during the measurement.

Based on the measurement data, a respective transfer function can be generated to relate true (i.e., known) wrinkle wavelength to measured wavelength for each reference standard (step 110). It is likely that the transfer function will be dependent on the distance from the surface to the wrinkle (i.e., wrinkle depth), since lateral heat transfer occurs preferentially in the plane of the part (e.g., in the CFRP fiber direction). All transfer functions are stored in the reference database (step 112).

After the reference database has been established, it can be referred to during IRT inspection of workpieces and parts made of composite material. For the purpose of illustration, IRT inspection of a panel made of composite material will now be described. Inspection of the panel follows the same procedure as for a reference standard, except the calibration information gathered with the reference standard will be used to disposition the wrinkle and assess whether it exceeds allowable limits or warrants further inspection with ultrasonic transducers.

Referring again to FIG. 8, the panel to be inspected is excited with a heat pulse by activating the flash lamps (step 114). The resulting thermal diffusion into the panel under test is then monitored by acquiring successive infrared images over time (step 116). Those raw infrared images can be processed in the same manner that the raw infrared images acquired from the reference standards were processed, e.g., using first- and second-time-derivative processing. Using either the first- or second-time-derivative image data, the wavelength of the wrinkles in each reference standard is measured using image processing tools to make the measurement in a well-known manner (step 118). Then a determination is made which transfer function to apply to the panel under test (step 120).

It is expected that the wavelength signal will become fuzzier with increasing depth. By measuring the time required to get the maximum contrast between the wrinkled area and the surrounding non-wrinkled area, one can estimate the depth of the wrinkle. With the depth information, one can determine which transfer function to use, for example, by inputting the wrinkle wavelength and wrinkle depth into a look-up table which correlates transfer functions with wrinkle depths, amplitudes and wavelengths.

Using the measured wavelength and estimated depth of the wrinkles in the panel and the selected transfer function, the actual (i.e., true) wrinkle wavelength in the panel can be calculated. For a given wrinkle wavelength, measured wavelength will likely increase with distance from the surface (i.e., with increasing depth). The actual wrinkle wavelength can be used to determine the disposition of the panel under test (step 122), e.g., whether the wrinkled region on the panel should undergo high-resolution ultrasonic inspection or not. In some cases, the actual wrinkle wavelength determined using infrared thermography may be sufficient to determine disposition of the part without need of ultrasonic inspection.

Even if IRT inspection is used without any quantitative capability, the speed at which an Infrared imaging system could screen a panel for wrinkles makes it an advantage—even if a separate high-resolution ultrasonic scan is performed to help quantify the wrinkle. (Such high-resolution ultrasonic scans are not currently performed and the traditional ultrasonic scans cannot detect wrinkles.) Currently available IRT equipment has fields of view of 16 to 36 square feet with acquisition times dependent on the maximum thickness of the panel to be inspected and with inspection times on the order of 130 seconds or less.

If a determination is made, based on the results of the IRT inspection, that the panel should also undergo high-resolution ultrasonic inspection in an area having wrinkles, an ultrasonic transducer array can be used to scan the identified region of interest to acquire ultrasonic image data. That ultrasonic image data can be processed to determine the amplitude of the wrinkle using the three-dimensional modeling technique disclosed in U.S. patent application Ser. No. 14/049,974, the disclosure of which is incorporated by reference herein in its entirety.

Using the results of IRT inspection, high-resolution ultrasonic inspection, or both, a determination can be made whether the panel has wrinkle dimensions which exceed the allowable values. There are allowable values for wrinkles. The values vary depending on the type of part. The typical allowables are described in terms of L/D (i.e., wavelength/amplitude). Panels having wrinkles characterized by an L/D ratio outside an allowable range may be rejected.

Even without direct measurement of amplitude, useful data can be obtained since the threshold wrinkle depth and wrinkle amplitude will provide threshold values for minimum detectable wavelength at the maximum detectable depth. It is likely the detectable wavelength will decrease as the wrinkle depth decreases.

Figure 9:
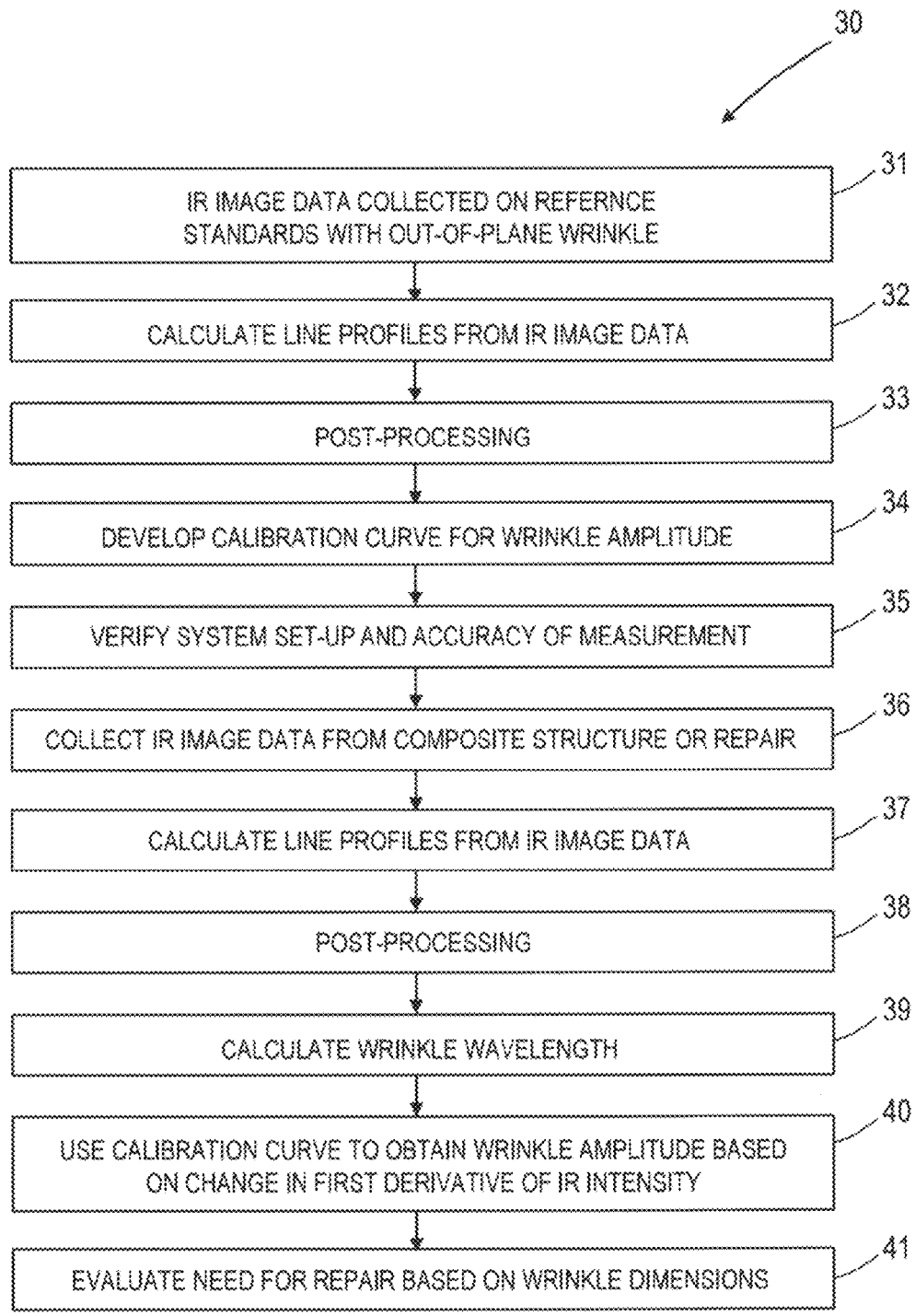
FIG. 9 is a flowchart identifying steps of a method for characterizing wrinkles using infrared thermography in accordance with another embodiment.

FIG. 9 is a block diagram identifying some components of a system for non-destructive inspection of large-scale composite structures in accordance with one architecture. Movements of the robot 64 (on which infrared cameras 4a, 4b and flash lamp 6 are mounted) are controlled by a robot control computer 70. Movements and firing of the laser tracker 24 are controlled by a laser tracking computer 136, which also receives laser tracking data from the laser tracker 24. Activation of the flash lamps 6 and activation of the infrared cameras 4a and 4b are controlled by an infrared thermography computer 8, which also receives infrared image data from the infrared cameras 4a and 4b. Activation of an ultrasonic transducer array 134 is controlled by an ultrasonic inspection control computer 130.

All of the computers can be in wireline or wireless communication with a master computer at an expert workstation 138. The master computer at the expert workstation 138 may be programmed to correlate the infrared image data with the laser tracking data and with the ultrasonic image data. The master computer may be further programmed to request 3-D model data from a 3-D model database server 142. In the case of thermographic wrinkle characterization, the master computer at the expert workstation 138 may also be programmed to request reference thermal signature data from a reference thermal signature database server 140.

The laser tracking computer 136 acquires location data for the infrared cameras 4a and 4b in a 3-D coordinate system of the composite structure. In the case of a barrel-shaped fuselage section, the infrared image data can be mapped directly onto a 3-D model of the fuselage section. The overlay of infrared image data with the 3-D model data enables improved data analysis and potential automated data analysis as well. For example, features/anomaly indications can be directly correlated to the fuselage structure by direct overlay of infrared image data on the 3-D model. In addition, the direct data overlay onto the model can be used to determine the thickness of a local area or spatial point. In one embodiment, the process involves application of infrared image data strips as one or more computer graphics texture maps, which are projected onto the 3-D model surfaces in a virtual environment displayed on a monitor or computer screen at the expert workstation 138.

In the embodiment depicted in FIG. 9, ultrasonic inspection is performed using an ultrasonic transducer array 134, which can be mounted on the end of an articulated arm of a robot similar to robot 64. The ultrasonic inspection system further comprises an ultrasonic pulser/receiver unit 132 which is operatively coupled to the ultrasonic transducer array 134 and encoding means (not shown). The ultrasonic pulser/receiver unit 132 is programmed to perform the following operations: sending control signals to the ultrasonic transducer array 134; receiving scan data signals from the ultrasonic transducer array 134; receiving X-Y position data signals from the encoding means; and correlating the scan data with the X-Y position data.

The ultrasonic inspection control computer 130 may comprise a general-purpose computer programmed with non-destructive inspection (NDI) scanning application software. The ultrasonic pulser/receiver unit 132 sends the encoder pulses to the NDI scanning software application, which interprets the encoder pulses as X- and Y-encoder values, which are used to position the scan data from the ultrasonic array 134 in the proper locations. The ultrasonic inspection control computer 130 can transmit ultrasonic image data to the expert workstation 138. The display may involve application of ultrasonic image data strips as one or more computer graphics texture maps, which are projected onto the 3-D model surfaces in a virtual environment displayed on a monitor or computer screen at the expert workstation 138.

In accordance with further embodiments of an infrared imaging system, the out-of-plane wrinkle wavelength measurement can come directly from the infrared thermographic image or thermography line profiles derived therefrom because the image and line profiles have a spatial dimension, whereas the maximum amplitude (i.e., height) of the out-of-plane wrinkle is determined using a calibration curve. This calibration curve is constructed by correlating infrared image data with optical measurement data.

FIG. 9 is a flowchart identifying steps of a method 30 for characterizing out-of-plane wrinkles in a composite structure and then evaluating the need for repair based on that characterization. In accordance with one embodiment, each wrinkle is characterized by determining one or more of the following wrinkle dimensions: wavelength, maximum amplitude and depth. The need for repair would then be evaluated by comparing the acquired wrinkle dimensions to various thresholds which establish allowable levels.

Prior to starting non-destructive testing of composite material, the infrared imaging system must be calibrated to enable measurement of wrinkle maximum amplitude. Referring to FIG. 9, infrared image data is collected from a multiplicity of reference standards consisting of composite material with out-of-plane wrinkles (step 31). The collected infrared image data is processed to obtain respective thermographic line profiles for intensity (I), first and second time derivatives of intensity ($dI/dt$ and $d^2I/dt^2$), and respective spatial derivatives ($d/dx(dI/dt)$) for respective reference standards (step 32). These thermographic line profiles then undergo appropriate post-processing (step 33), such as smoothing or filtering. Those same reference standards are later cut to expose cross sections of the composite material with wrinkles, which cross sections are imaged using a microscope. The resulting photographs or digital images are measured using image processing software. The resulting optical cross-sectional measurement data is then correlated with selected thermographic line profile data corresponding to the same area where the reference standards were sectioned to develop a calibration curve for wrinkle amplitude (step 34). Thereafter the system set-up and the accuracy of the wrinkle amplitude measurements obtained from the infrared image data are verified (step 35).

The methodology disclosed herein enables the calibration of infrared imaging systems through the use of optical cross-sectional measurement data from reference standards. By basing calibration on an optically measured reference standard, it is possible to pull more data into location-specific inspections.

The term "reference standards" should be construed broadly to include coupons or parts made for reference purposes and early production parts fabricated for evaluation. As previously noted, the typical practice is to cross section a first part produced by the production line and sometimes a second production part in order to understand manufacturing problems (this may be part of a production part verification process). However, the sectioning and micrographing is not done for parts made after that. The process disclosed herein is equally applicable to early production parts.

Upon completion of the calibration process 34, the calibrated infrared imaging system can be used to non-destructively inspect a composite structure or repair. Infrared image data is collected from the composite structure or repair (step 36). The composite structure may be a part in production or a part in service (e.g., part of an aircraft or other vehicle). The part to be inspected may have been previously repaired or not. The collected intensity values are processed to obtain respective thermographic line profiles comprising intensity, first and second time derivatives of the intensity, and spatial derivatives (step 37). These thermographic line profiles then undergo appropriate post-processing (step 38), such as smoothing or filtering. The thermographic line profiles can be displayed on a graph as Y values versus pixel values along the X axis. The data contained in these thermographic line profiles is used to calculate wrinkle wavelength in terms of number of pixels, which number is then converted into inches or some other dimensional unit of distance (step 39). Thereafter the calibration curve is used to obtain wrinkle maximum amplitude based on a change in the thermography line profile data, such as a change in the first time derivative of the infrared intensity values (step 40). The need for repair is then evaluated by comparing the acquired wrinkle dimensions to corresponding thresholds representing maximum allowable values (step 41). If a wrinkle dimension exceeds a threshold, the composite structure under inspection can be designated for repair or further evaluation.

To illustrate the calibration, exemplary calculations based on intensity and first time derivative data and optical measurement data acquired from two coupons, one wrinkle-free and the other wrinkled, will now be described and shown in FIGS. 10A and 10B. First, a coupon A1 made of "wrinkle-free" (i.e., free of critical out-of-plane wrinkles) composite material 20 (with plies 22*a*, 22*b* and 22*c* indicated by lines) and a coupon A2 made of wrinkled composite material 20' (with plies 22*d* and 22*e* indicated by lines) were subjected to infrared imaging. The acquired infrared image data was stored in a non-transitory tangible computer-readable storage medium. Then coupons A1 and A2 were sectioned and optically inspected. FIG. 10A is a diagram representing a micrograph of a portion of the sectioned "wrinkle-free" composite material of coupon A1. In contrast, FIG. 10B is a diagram representing a micrograph of sectioned composite material in coupon A2 having out-of-plane wrinkles. Both micrographs have boundary lines superimposed thereon, which boundary lines represent estimated interfaces between plies.

No critical out-of-plane wrinkles (e.g., an out-of-plane wrinkle having a maximum amplitude D>0.003 inch) were observed in coupon A1. In contrast, coupon A2 had a wrinkle which was measured using an image processing software application. In this case, four points were manually selected by a technician or other trained inspector (indicated by respective solid circles in FIG. 10B) on a display screen: two of which represent the termination points of a wave-shaped out-of-plane wrinkle having a wavelength L and two of which correspond to the maximum amplitude D of that same wrinkle. After these points had been selected, the technician activated the image processing software application, which then measured the wavelength and maximum amplitude. (In the alternative, the measurements can be done manually.) In this instance, the optical wrinkle measurements were L=0.217 inch and D=0.0110 inch, resulting in a ratio L/D=19.6.

Figure 11:
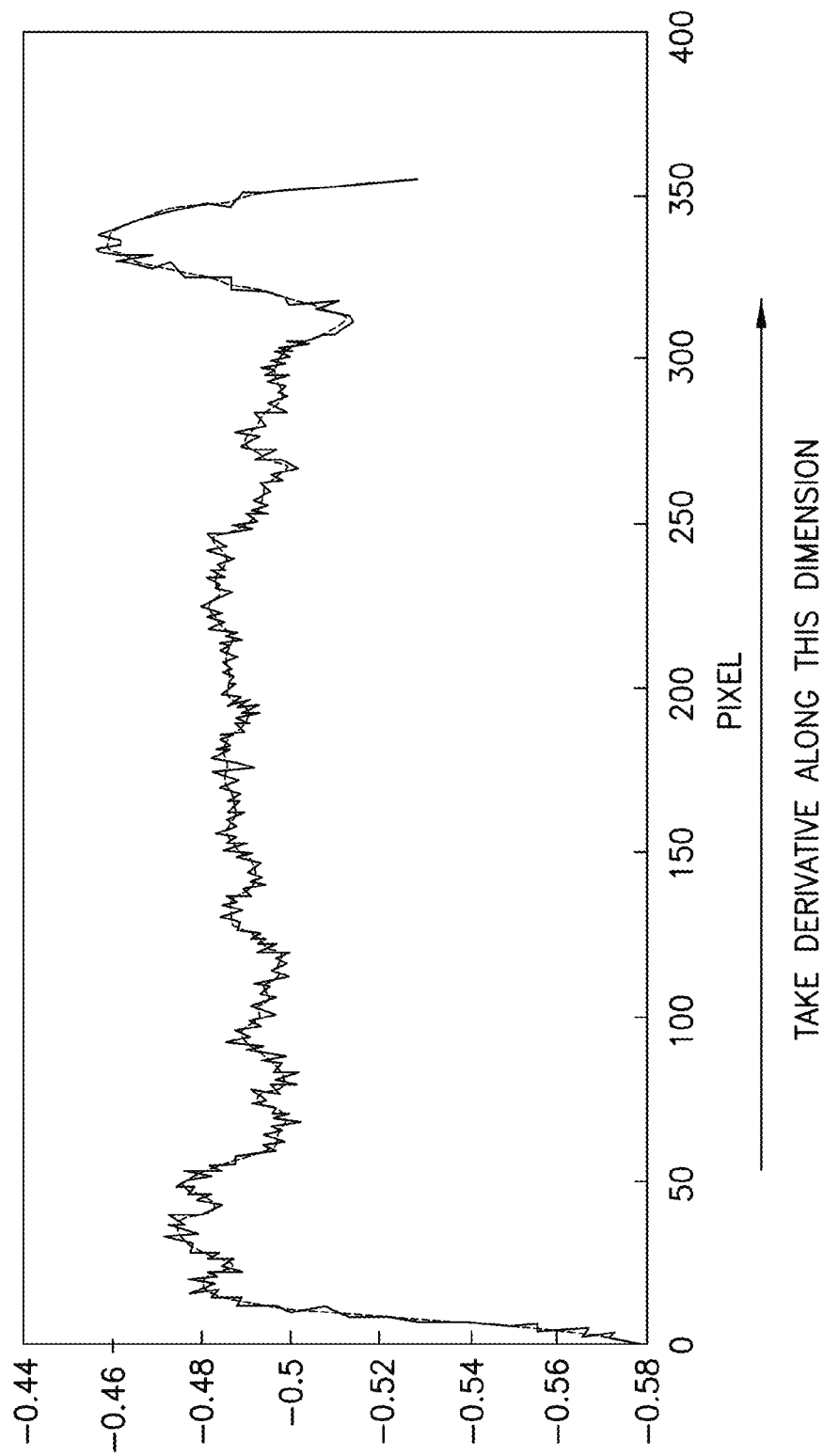
FIG. 11 is a graph of the first time derivative of the intensity (Y axis) versus pixel position (X axis) across the wrinkle-free coupon A1 at a first instant in time. The raw data is indicated by a solid line, while the smoothed data is indicated by a dashed line.
Figure 12:
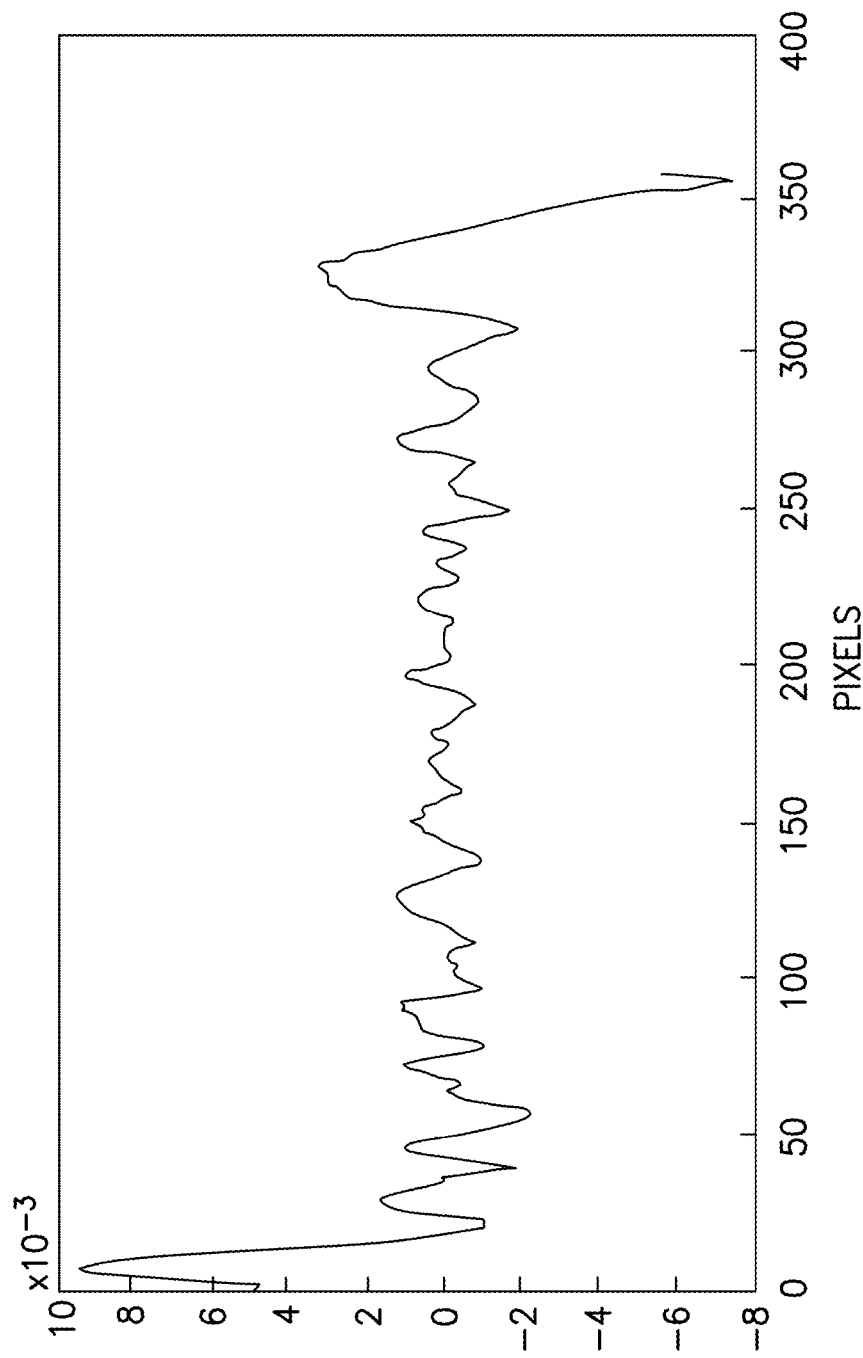
FIG. 12 is a graph of the spatial derivative of the first time derivative seen in FIG. 11 versus pixel position across the coupon.

In addition to the optical measurements, the stored infrared image data was processed to generate thermographic line profiles. The first time derivative of the intensity produced at various pixel positions in coupon A1 at a time of 1.751 seconds is depicted in FIG. 11. The raw data is indicated by a solid line, while the smoothed data is indicated by a dashed line in FIG. 11. The spatial derivative of the smoothed data was then calculated along the pixel (i.e., X) dimension. FIG. 12 is a graph of the spatial derivative of the smoothed first time derivative seen in FIG. 11 versus pixel position across wrinkle-free coupon A1. Similar thermographic line profiles were obtained from wrinkled coupon A2.

One method used to determine the wrinkle wavelength in coupon A2 (described above) was optical measurement of a portion of the sectioned coupon A2. The other method involved finding peaks or valleys in the thermographic line profiles acquired from the same wrinkled region. The distance between adjacent peaks or valleys is equal to the wrinkle wavelength. A correction factor is applied to this measured distance in order to account for the resolution of the infrared imaging system. Then, within the area defined as the wrinkle wavelength, a change in the thermographic line profile data (e.g., first time derivative of intensity) is calculated. Based on the results of this calculation, a calibration curve is developed. This calibration curve is configured to relate the change in the thermographic line profile data to the optical measurement for the maximum amplitude (i.e., height) of the out-of-plane wrinkle.

Figure 13A:
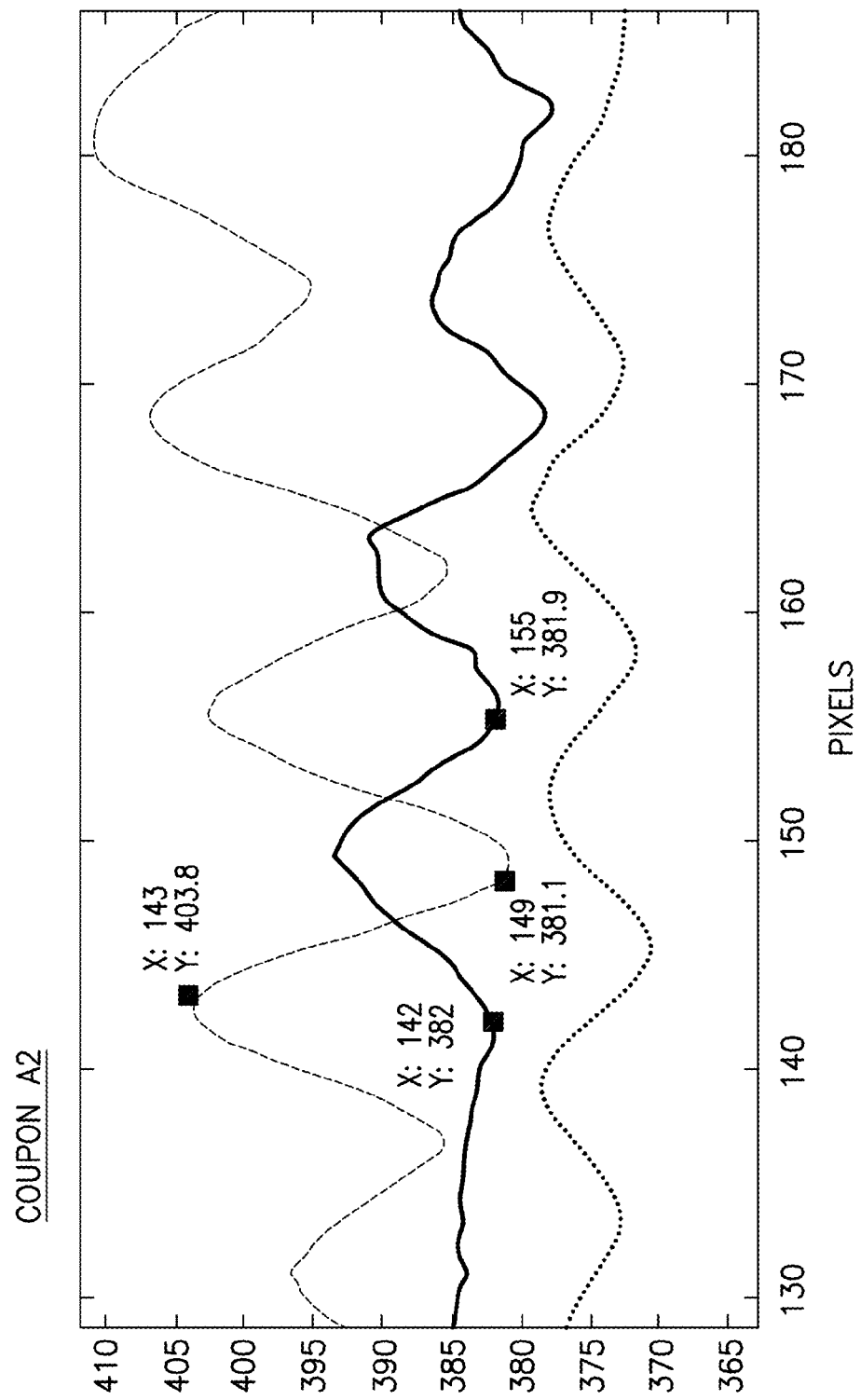
FIG. 13A is a graph of the intensity (solid line), first time derivative (dashed line) and spatial derivative (dotted line) versus pixel position (X axis) across the wrinkled coupon A2 at an instant in time.
Figure 13B:
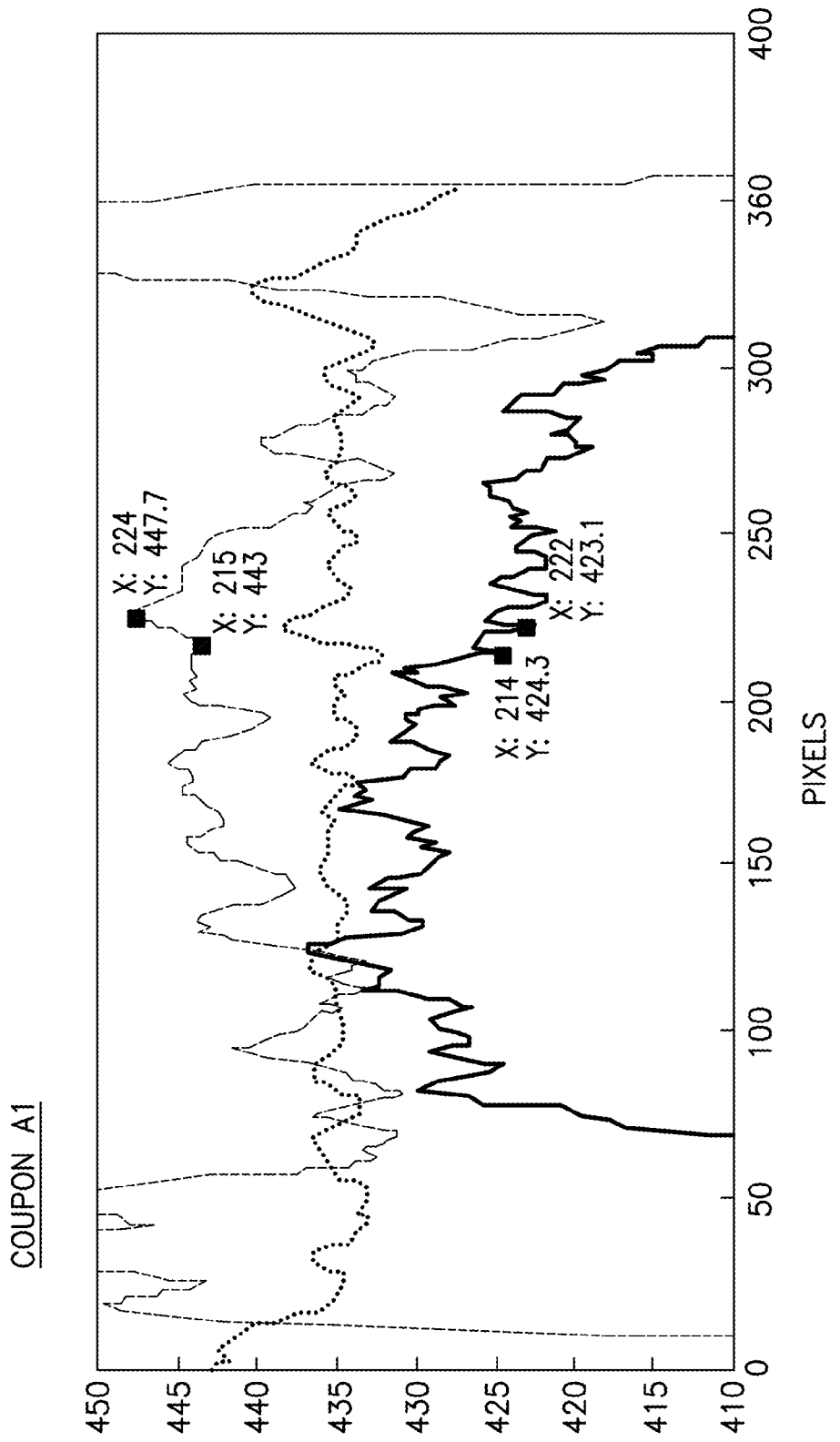
FIG. 13B is a graph of the intensity (solid line), first time derivative (dashed line) and spatial derivative (dotted line) versus pixel position (X axis) across the wrinkle-free coupon A1 at an instant in time.

One technique for developing such a calibration curve using intensity and its first time derivative will now be described with reference to FIGS. 13A and 13B for the purpose of illustration. FIG. 13A is a graph of the intensity (solid line), first time derivative (dashed line) and spatial derivative (dotted line) versus pixel position (X axis) across the wrinkled coupon A2 at an instant in time. FIG. 13B is a graph of the intensity (solid line), first time derivative (dashed line) and spatial derivative (dotted line) versus pixel position (X axis) across the wrinkle-free coupon A1 at an instant in time. However, it should be appreciated a calibration curve can be developed using the second time derivative or a spatial derivative instead of the first time derivative. [Note: Each line was scaled and offset so that all three lines would show on the same graph.]

FIG. 13A has two pairs of points, each point having X and Y coordinates. Points (X: 142, Y: 382) and (X: 155, Y: 381.9) lie in valleys along the intensity line profile, whereas points (X: 143, Y: 403.8) and (X: 148, Y: 381.1) lie along the first time derivative line profile. In this example, the spacing for each pixel in the infrared image is 0.02 inch. Treating points (X: 142, Y: 382) and (X: 155, Y: 381.9) as corresponding to the termination points of one wrinkle wavelength, the wavelength L can be computed as L=(155−142)*0.02=0.260 inch. In addition, because the maximum amplitude D is proportional to the change in the first time derivative dI/dt, one can use points (X: 143, Y: 403.8) and (X: 148, Y: 381.1) to compute dI/dt=403.8−381=22.8=Δ(dI). In contrast, the corresponding optical measurements were L=0.2192 inch and D=0.0106 inch.

Similarly, FIG. 13B has two pairs of points, each point having X and Y coordinates. Points (X: 214, Y: 424.8) and (X: 222, Y: 423.1) lie in valleys along the intensity line profile, whereas points (X: 215, Y: 443) and (X: 224, Y: 447.7) lie along the first time derivative line profile. Treating points (X: 214, Yr 424.8) and (X: 222, Yr 423.1) as corresponding to the termination points of a distortion, the length L of this distortion can be computed as L=(222−214)*0.02=0.16 inch. In addition, one can use points (X: 215, Y: 443) and (X: 224, Yr 447.7) to compute dI/dt=447.7−443=4.7. (Even though there is an L measurement, D is small, so this really is not a wrinkle, but instead provides a baseline value for the calibration. The points were selected so that the distortion in coupon A1 had a length reasonably close to the length for the wrinkle in coupon A2 and with a noticeable change in dI/dt (which is the parameter being tied to the maximum amplitude).

The resulting linear relationship between the actual maximum amplitude of the wrinkle and the change in the first time derivative of the intensity would be $D_{actual} = (\Delta(dI) - 4.7) * C$, where the conversion factor $C = 0.0106/(22.8 - 4.7)$. In the alternative, a calibration curve that is not linear could be employed.

Characterization of in-Plane Wrinkles

In accordance with additional embodiments, the wavelength and maximum amplitude of an in-plane wrinkle can be measured directly from thermography line profiles because the infrared image has spatial dimensions (i.e., wavelength and maximum amplitude) in the X and Y directions.

Figure 14:
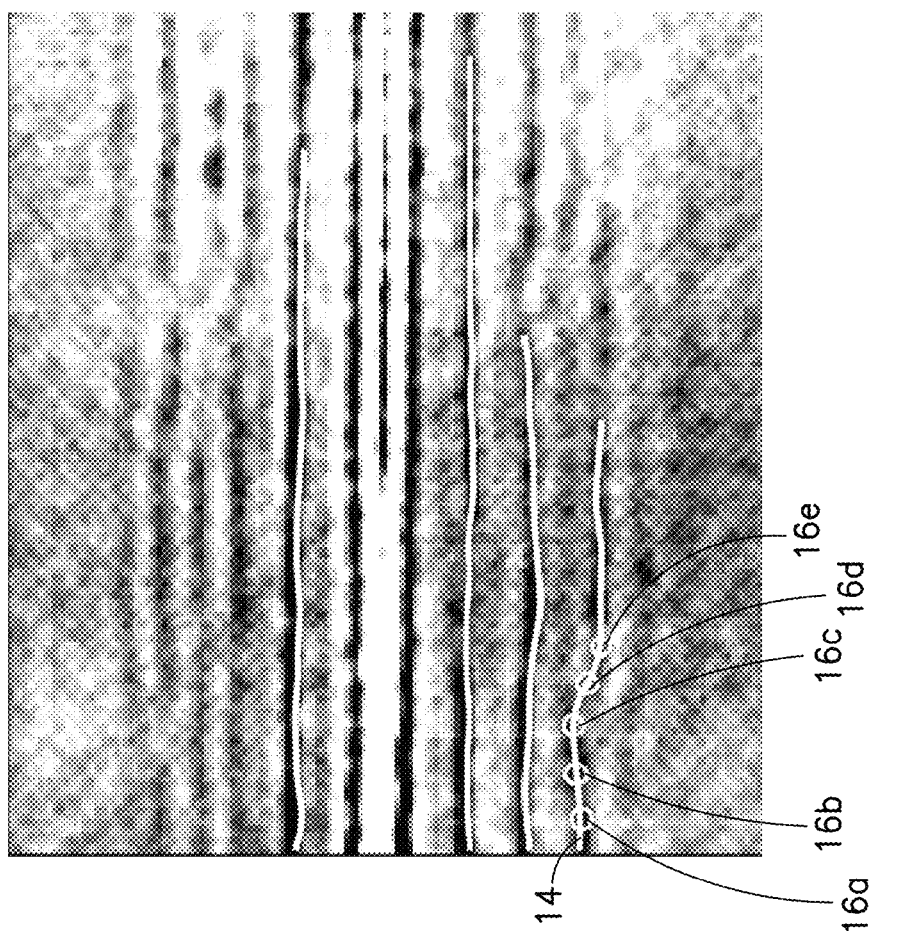
FIG. 14 is a portion of an infrared image of a coupon made of composite material having an in-plane wrinkle with superimposed lines that trace the path of various fibers.

FIG. 14 shows the result when a raw infrared image of a coupon made of composite material having an in-plane wrinkle undergoes first-time-derivative processing. The first-time-derivative image seen in FIG. 14 has superimposed lines that trace the path of various fibers. More specifically, the in-plane wrinkle has a line 14 superimposed thereon. Respective circles 16a through 16e placed along line 14 in turn correspond to respective points selected by a technician, which points will be used by the image processing software application to compute the wavelength L and maximum amplitude D of the traced in-plane wrinkle based on measurements made in the plane of the part. In addition, the depth of the in-plane wrinkle could be determined from the time that the wrinkle signature appears on the processed infrared images. There is some imprecision in the actual depth determination, as a function of the time, but would be adequate for any subsequent repair approach.

It should also be appreciated that the plies from each layer do not cross. The only way the in-plane wrinkle forms is if the density of fibers, i.e., the concentration of the epoxy matrix, changes. As noted, it is this change in fiber/resin ratio that results in a change in the thermographic response.

In the image presented in FIG. 14, one can see plies at two different 45-degree offsets in the wrinkle image. The lines look straight at ±45 degrees because there are no wrinkles. The image has been optimized at a time to see the wrinkles near the surface. If there were wrinkles in the ±45 deeper plies, one would need to look at a later time image to optimize the wrinkle signature.

In accordance with one embodiment, the lines are superimposed on the image by an automated process using a software application configured to perform a line finding algorithm (described in more detail below) that is dependent on contrast changes. Alternatively, the trace lines could be drawn manually by a technician by dragging a cursor.

In accordance with one embodiment, the method for characterizing an in-plane wrinkle in a composite material comprises the following steps: (1) the color scale of the first-time-derivative image is inverted and the contrast is enhanced; (2) the processed image is rotated and cropped to isolate the area of interest; (3) then the area of interest from the processed image is converted into a binary image; (4) then the line finding algorithm is used to find lines representing fibers in a plane; and (5) the found lines are overlaid onto the first-time-derivative image. (The same process can be performed using the intensity image.)

The general process for finding lines from the binary image is as follows: Start on the left side of first-time-derivative (or intensity) image. In the first column, find pixels that are a 1 (bright). For example, assume that the coordinates of the line of interest are x=0, y=138. For each pixel, look to the next pixel to the right (i.e., x=1, y=138) to see if it is a 1. If not, look a certain range (user specified) above and below. For example, if one were to look in a range of 4, one would be looking at the pixels for x=1, y=134 to 142 to see if there are any pixels that are 1. If a neighboring pixel is found, mark the found pixel and go back to the initial step with the new pixel found. If no neighboring pixel is found, one can guess that x=1, y=138 is the next pixel and go back to the initial step and continue searching to the right (i.e., x=2, y=138). The technician may keep track that no pixel was found and only allow a certain number of consecutive missed pixels. If the number of consecutive missed pixels reaches a user-defined number, the line searching stops.

Based on the observable characteristics of the lines superimposed on the first-time-derivative image (or the intensity image), a technician may detect the possible presence of an out-of-plane or in-plane wrinkle and then determine that it is a wrinkle feature that should be considered during analysis to determine whether it will cause a detrimental weakness of the structure. Since the CFRP laminate structure is weakened when the fibers are not straight (since the epoxy matrix then has to take the load) whether the wrinkle is in plane or out of plane, it does not matter.

Figure 15:
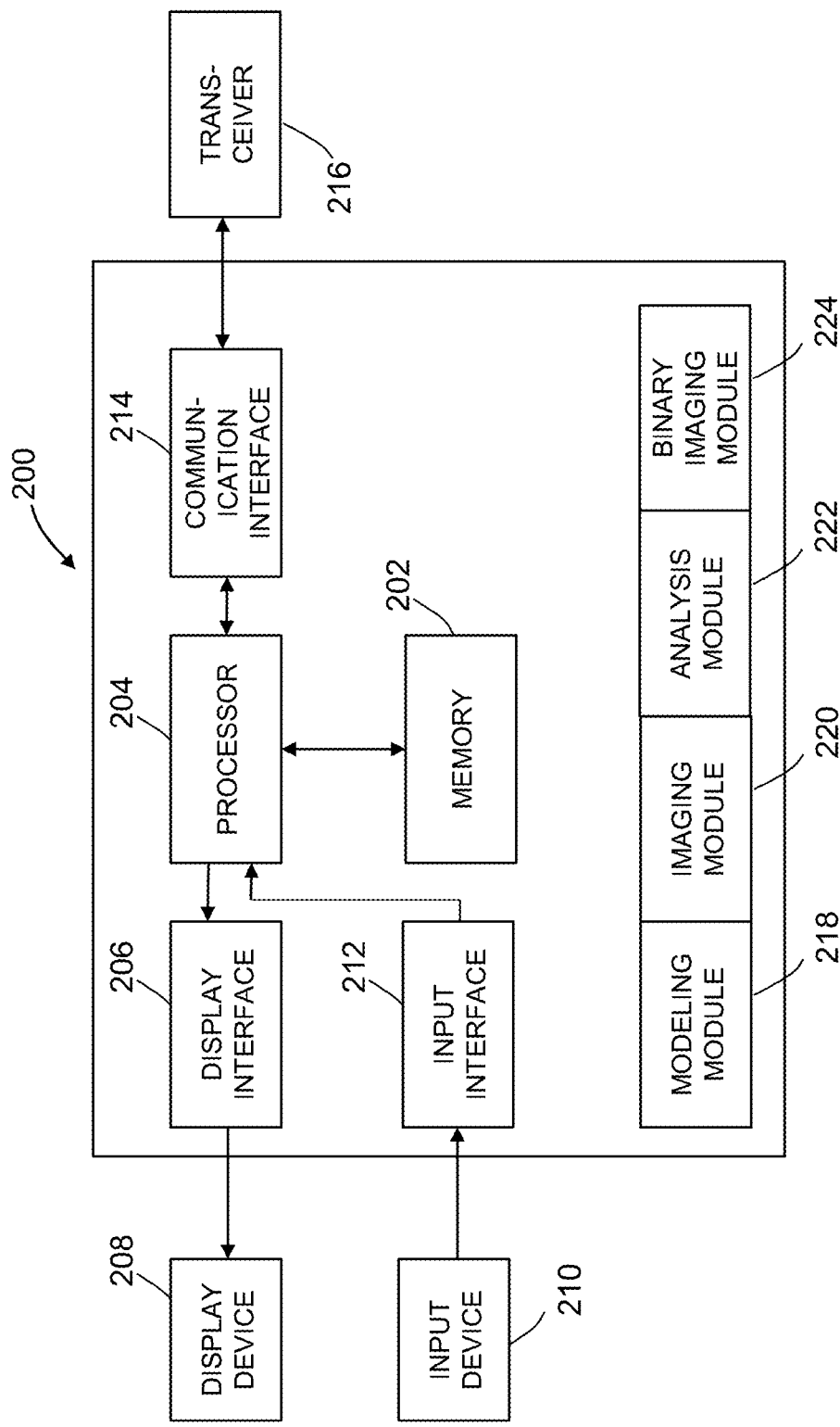
FIG. 15 is a block diagram identifying components of a computer system suitable for executing automated data processing functions adapted to predict the performance of a wrinkled composite structure.

FIG. 15 is a block diagram identifying components of a computer system 200 suitable for executing automated data processing functions adapted to predict the performance of a wrinkled composite structure. In accordance with one embodiment, computer system 200 comprises a memory device 202 and a processor 204 coupled to memory device 202 for use in executing instructions. More specifically, computer system 200 is configurable to perform one or more operations described herein by programming memory device 202 and/or processor 204. For example, processor 204 may be programmed by encoding an operation as one or more executable instructions and by providing the executable instructions in memory device 202.

Processor 204 may include one or more processing units (e.g., in a multi-core configuration). As used herein, the term "processor" is not limited to integrated circuits referred to in the art as a computer, but rather broadly refers to a controller, a microcontroller, a microcomputer, a programmable logic controller, an application specific integrated circuit, and other programmable circuits.

In the exemplary embodiment, memory device 202 includes one or more devices (not shown) that enable information such as executable instructions and/or other data to be selectively stored and retrieved. In the exemplary embodiment, such data may include, but is not limited to, properties of composite materials, properties of ultrasonic waves, modeling data, image data, calibration curves, operational data, and/or control algorithms. In the exemplary embodiment, computer system 200 is configured to automatically implement a parametric finite element analysis to determine a desired evaluation setting for use in inspecting a wrinkled composite structure. Alternatively, computer system 200 may use any algorithm and/or method that enables the methods and systems to function as described herein. Memory device 202 may also include one or more non-transitory tangible computer-readable storage media, such as, without limitation, dynamic random access memory, static random access memory, a solid state disk, and/or a hard disk.

In the exemplary embodiment, computer system 200 further comprises a display interface 206 that is coupled to processor 204 for use in presenting information to a user. For example, display interface 206 may include a display adapter (not shown) that may couple to a display device 208, such as, without limitation, a cathode ray tube, a liquid crystal display, a light-emitting diode (LED) display, an organic LED display, an "electronic ink" display, and/or a printer.

Computer system 200, in the exemplary embodiment, further comprises an input interface 212 for receiving input from the user. For example, in the exemplary embodiment, input interface 212 receives information from an input device 210 suitable for use with the methods described herein. Input interface 212 is coupled to processor 204 and to input device 210, which may include, for example, a joystick, a keyboard, a pointing device, a mouse, a stylus, a touch sensitive panel (e.g., a touch pad or a touch screen), and/or a position detector.

In the exemplary embodiment, computer system 200 further comprises a communication interface 214 that is coupled to processor 204. In the exemplary embodiment, communication interface 214 communicates with at least one remote device, e.g., a transceiver 216. For example, communication interface 214 may use, without limitation, a wired network adapter, a wireless network adapter, and/or a mobile telecommunications adapter. A network (not shown) used to couple computer system 200 to the remote device may include, without limitation, the Internet, a local area network (LAN), a wide area network, a wireless LAN, a mesh network, and/or a virtual private network or other suitable communication means.

In the exemplary embodiment, computer system 200 further comprises at least a modeling module 218, an imaging module 220, an analysis module 222 and a binary imaging module 224 that enable the methods and systems to function as described herein. These modules may take the form of software comprising code executed by the processor 204. The modeling module 218 is configured to generate finite element models of the wrinkled composite structure. The imaging module 220 is configured to produce and process images such as micrographs and infrared images. The analysis module 222 is configured to perform a FEM failure analysis of the finite element model by applying boundary conditions and loads.

Figure 16:
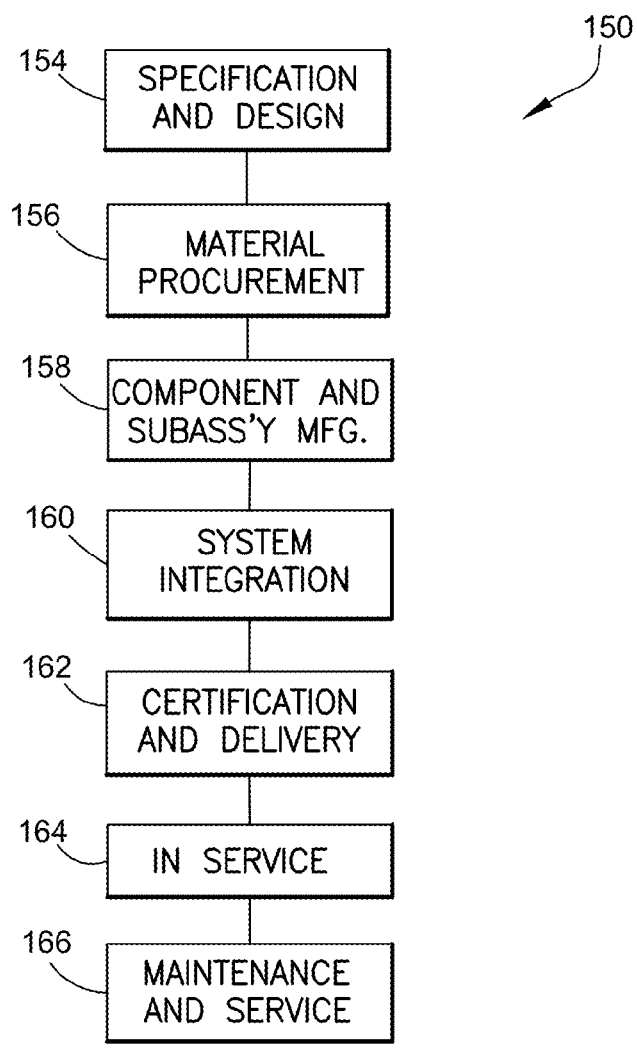
FIG. 16 is a flow diagram of an aircraft production and service methodology.
Figure 17:
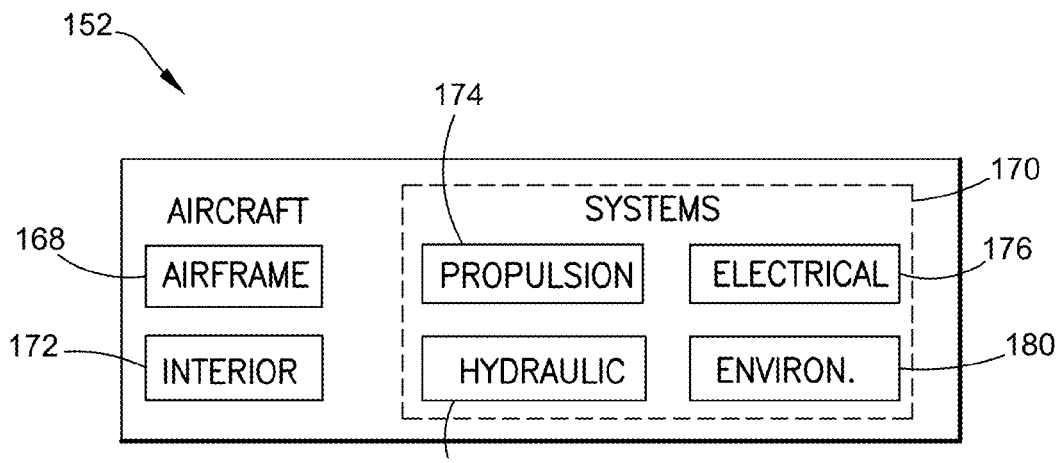
FIG. 17 is a block diagram showing systems of an aircraft.

The systems and methods disclosed above may be employed in an aircraft manufacturing and service method 150 as shown in FIG. 16 for inspecting parts of an aircraft 152 as shown in FIG. 17. During pre-production, exemplary method 150 may include specification and design 154 of the aircraft 152 and material procurement 156. During production, component and subassembly manufacturing 158 and system integration 160 of the aircraft 152 takes place. Thereafter, the aircraft 152 may go through certification and delivery 162 in order to be placed in service 164. While in service by a customer, the aircraft 152 is scheduled for routine maintenance and service 166 (which may also include modification, reconfiguration, refurbishment, and so on).

Each of the processes of method 150 may be performed or carried out by a system integrator, a third party, and/or an operator (e.g., a customer). For the purposes of this description, a system integrator may include without limitation any number of aircraft manufacturers and major-system subcontractors; a third party may include without limitation any number of venders, subcontractors, and suppliers; and an operator may be an airline, leasing company, military entity, service organization, and so on.

As shown in FIG. 17, the aircraft 152 produced by exemplary method 150 may include an airframe 168 (comprising, e.g., a fuselage, frames, stiffeners, wing boxes, etc.) with a plurality of systems 170 and an interior 172. Examples of high-level systems 170 include one or more of the following: a propulsion system 174, an electrical system 176, a hydraulic system 178, and an environmental control system 180. Any number of other systems may be included. Although an aerospace example is shown, the principles disclosed herein may be applied to other industries, such as the automotive industry.

Apparatus and methods embodied herein may be employed during any one or more of the stages of the production and service method 150. For example, components or subassemblies fabricated or assembled during production process 158 may be inspected using the infrared imaging system disclosed herein. Also, one or more apparatus embodiments, method embodiments, or a combination thereof may be utilized during the production stages 158 and 160, for example, by substantially expediting nondestructive inspection of or reducing the cost of an aircraft 152. Similarly, one or more of apparatus embodiments, method embodiments, or a combination thereof may be utilized while the aircraft 152 is in service, for example and without limitation, during maintenance and service 166.

While infrared thermographic inspection methods have been described with reference to various embodiments, it will be understood by those skilled in the art that various changes may be made and equivalents may be substituted for elements thereof without departing from the scope of the teachings herein. In addition, many modifications may be made to adapt the teachings herein to a particular situation without departing from the scope thereof. Therefore it is intended that the claims not be limited to the particular embodiments disclosed herein.

The process claims set forth hereinafter should not be construed to require that the steps recited therein be performed in alphabetical order (any alphabetical ordering in the claims is used solely for the purpose of referencing previously recited steps) or in the order in which they are recited unless the claim language explicitly specifies or states conditions indicating a particular order in which some or all of those steps are performed. Nor should the process claims be construed to exclude any portions of two or more steps being performed concurrently or alternatingly unless the claim language explicitly states a condition that precludes such an interpretation.

The invention claimed is:

1. A method for non-destructive inspection of composite structures, comprising:
   (a) developing a calibration curve for an infrared imaging system based on correlation of infrared image data and optical cross-section measurement data acquired from reference standards made of composite material, at least some of the reference standards having at least one wrinkle;
   (b) collecting infrared image data from a part made of composite material using the infrared imaging system after completion of step (a);
   (c) detecting the presence of an out-of-plane wrinkle in the part based on the infrared image data collected in step (b);
   (d) generating thermographic line profile data based on the infrared image data;
   (e) measuring a wavelength of the out-of-plane wrinkle in the part based on the thermographic line profile data generated in step (d); and
   (f) measuring an amplitude of the out-of-plane wrinkle in the part by applying the calibration curve to the thermographic line profile data generated in step (d).

2. The method as recited in claim 1, further comprising:
   (g) determining if the part is acceptable based on the measured wavelength and amplitude; and
   (h) designating the part for repair or further evaluation in response to a determination in step (g) that the part is not acceptable.

3. The method as recited in claim 2, further comprising calculating a wrinkle wavelength-to-amplitude ratio using the measured wavelength and amplitude of the out-of-plane wrinkle, wherein step (g) comprises determining if the wrinkle wavelength-to-amplitude ratio is outside an allowable range.

4. The method as recited in claim 1, wherein step (d) comprises calculating a time derivative of the infrared image data.

5. The method as recited in claim 1, wherein step (d) comprises calculating a spatial derivative of the infrared image data.

6. The method as recited in claim 1, wherein step (a) comprises:
   collecting infrared image data from first and second reference standards made of composite material, wherein the first reference standard is wrinkle-free and the second reference standard has at least one wrinkle;
   generating thermographic line profile data based on the infrared image data acquired from the first and second reference standards;
   calculating changes in the thermographic line profile data along respective lines in the first and second reference standards;
   calculating a difference between the respective changes in the thermographic line profile data;
   cutting the first and second reference standards to expose cross sections, wherein the cross section of the second reference standard intersects the wrinkle;
   imaging the exposed cross sections of the first and second reference standards to produce respective optical cross sections;
   measuring an amplitude of the wrinkle which appears in the optical cross section of the second reference standard; and
   calculating a conversion factor based on the calculated difference and the measured amplitude; and
   constructing a calibration curve using the conversion factor.

7. The method as recited in claim 6, wherein the changes in the first and second thermographic line profile data are differences between respective time derivatives of intensity at respective spatial points along the lines in the first and second reference standards.

8. The method as recited in claim 6, wherein the changes in the first and second thermographic line profile data are differences between respective spatial derivatives at respective spatial points along the lines in the first and second reference standards.

9. A method for measuring an out-of-plane wrinkle in a structure made of a composite material, the method comprising:
   (a) developing a calibration curve for an infrared imaging system based on correlation of infrared image data and optical cross-section measurement data acquired from reference standards made of composite material, at least some of the reference standards having at least one wrinkle;
   (b) acquiring infrared image data from an inspected area on a surface of the structure using an infrared camera of the infrared imaging system, the infrared image data being indicative of the presence of an out-of-plane wrinkle under the surface of the inspected area;
   (c) generating thermographic line profile data based on the infrared image data;
   (d) processing the thermographic line profile data to estimate a value of a first wrinkle dimensional parameter of the out-of-plane wrinkle;
   (e) processing the thermographic line profile data to estimate a value of a second wrinkle dimensional parameter of the out-of-plane wrinkle based in part on the calibration curve;
   (f) calculating a value of a wrinkle parameter which is a function of the first and second wrinkle dimensional parameters; and
   (g) determining a status of the composite structure in dependence on whether the value of the wrinkle parameter calculated in step (f) is inside or outside an allowable range of values.

10. The method as recited in claim 9, wherein step (c) comprises calculating a time derivative of the infrared image data.

11. The method as recited in claim 9, wherein step (c) comprises calculating a spatial derivative of the infrared image data.

12. The method as recited in claim 9, wherein the first wrinkle dimensional parameter is wrinkle wavelength, the second wrinkle dimensional parameter is wrinkle maximum amplitude, and the wrinkle parameter is a ratio of the wrinkle wavelength to the wrinkle maximum amplitude.

13. A method for measuring an in-plane wrinkle in a composite structure, comprising:
   (a) moving an infrared camera to a location whereat a field of view of the infrared camera encompasses an inspection area on a surface of the composite structure;
   (b) activating at least one flash lamp to output light that illuminates at least portions of the inspection area;
   (c) activating the infrared camera to acquire infrared image data while the field of view of the infrared camera encompasses at least the inspection area;
   (d) processing the infrared image data to identify selected points along an in-plane wrinkle; and
   (e) determining a wavelength and a maximum amplitude of the in-plane wrinkle based on the selected points using image processing software.

14. The method as recited in claim 13, wherein the infrared image data comprises values representing a time derivative of intensity values at respective spatial points in the inspection area.

15. The method as recited in claim 13, wherein the infrared image data comprises values representing a spatial derivative of intensity values or time derivative values at respective spatial points in the inspection area.

16. A method for calibrating an infrared imaging system, comprising:
   (a) forming a first reference standard made of a type of composite material and having a wrinkle;
   (b) forming a second reference standard made of the same type of composite material and not having a wrinkle;
   (c) collecting first infrared image data from the first reference standard;
   (d) collecting second infrared image data from the second reference standard;
   (e) generating first thermographic line profile data based on the first infrared image data;
   (f) generating second thermographic line profile data based on the first infrared image data;
   (g) calculating a change in the first thermographic line profile data along a line in the first reference standard;
   (h) calculating a change in the second thermographic line profile data along a line in the second reference standard;
   (i) calculating a difference between the respective changes;

(j) cutting the first and second reference standards to expose cross sections, wherein the cross section of the first reference standard intersects the wrinkle;

(k) imaging the exposed cross sections of the first and second reference standards to produce respective optical cross sections;

(l) measuring an amplitude of the wrinkle which appears in the optical cross section of the first reference standard;

(m) calculating a conversion factor based on the difference calculated in step (i) and the amplitude measured in step (l); and (n) constructing a calibration curve using the conversion factor.

17. The method as recited in claim 16, wherein the changes in the first and second thermographic line profile data are differences between respective time derivatives of intensity at respective spatial points along the lines in the first and second reference standards.

18. The method as recited in claim 16, wherein the changes in the first and second thermographic line profile data are differences between respective spatial derivatives at respective spatial points along the lines in the first and second reference standards.

19. An infrared imaging system comprising a computer configured to convert infrared image data to a wrinkle maximum amplitude measurement value based on a calibration curve that correlates infrared image data indicative of an out-of-plane wrinkle to optical cross-section measurement data indicative of an out-of-plane wrinkle.

20. The infrared imaging system as recited in claim 19, wherein converting the infrared image data to the wrinkle maximum amplitude measurement value comprises generating thermographic line profile data based on the infrared image data and then processing the thermographic line profile data to estimate the wrinkle maximum amplitude measurement value based in part on the calibration curve.

* * * * *